(12) United States Patent
Lavedas

(10) Patent No.: US 9,812,790 B2
(45) Date of Patent: Nov. 7, 2017

(54) NEAR-FIELD GRADIENT PROBE FOR THE SUPPRESSION OF RADIO INTERFERENCE

(71) Applicant: Raytheon Company, Waltham, MA (US)

(72) Inventor: Thomas G. Lavedas, Clifton, VA (US)

(73) Assignee: RAYTHEON COMPANY, Waltham, MA (US)

( * ) Notice: Subject to any disclaimer, the term of this patent is extended or adjusted under 35 U.S.C. 154(b) by 179 days.

(21) Appl. No.: 14/677,130

(22) Filed: Apr. 2, 2015

(65) Prior Publication Data

US 2015/0372395 A1    Dec. 24, 2015

Related U.S. Application Data

(60) Provisional application No. 62/015,679, filed on Jun. 23, 2014.

(51) Int. Cl.
*H01Q 21/28* (2006.01)
*H01Q 1/52* (2006.01)
(Continued)

(52) U.S. Cl.
CPC ............. *H01Q 21/28* (2013.01); *H01Q 1/521* (2013.01); *H01Q 7/005* (2013.01); *H01Q 7/02* (2013.01)

(58) Field of Classification Search
CPC .......... H01Q 21/28; H01Q 1/521; H01Q 7/02; H01Q 7/005
See application file for complete search history.

(56) References Cited

U.S. PATENT DOCUMENTS

| 3,774,221 A | 11/1973 | Francis |
| 3,823,403 A | 7/1974 | Walter et al. |

(Continued)

FOREIGN PATENT DOCUMENTS

| JP | H11-313017 | 11/1999 |
| WO | WO 2006/107862 A2 | 10/2006 |
| WO | WO 2010/002821 A1 | 1/2010 |

OTHER PUBLICATIONS

U.S. Appl. No. 13/027,434, filed Feb. 15, 2011, Lavedas.
(Continued)

*Primary Examiner* — Dieu H Duong
*Assistant Examiner* — Michael Bouizza
(74) *Attorney, Agent, or Firm* — Daly, Crowley, Mofford & Durkee, LLP

(57) ABSTRACT

An antenna system is provided comprising first, second, and third loop antennas, each antenna having a respective loop area and spaced apart from the other antennas. The first and third antennas are configured and driven to form a first independent balanced feed point that is substantially isolated from the second antenna, which is configured to be driven from a second balanced feed point. A sum of the first and second respective loop areas, at a sum port in operable communication with the first and second balanced feed points, is substantially equivalent to the third respective loop area. An automatic control system is configured to automatically and independently adjust, via the balanced feed points, at least one of amplitude and phase for at least one of the three loop antennas, to help to substantially maximize suppression of RFI for a sum of signals from the first and second balanced feed points.

20 Claims, 8 Drawing Sheets

(51) Int. Cl.
*H01Q 7/00* (2006.01)
*H01Q 7/02* (2006.01)

(56) References Cited

U.S. PATENT DOCUMENTS

| | | | |
|---|---|---|---|
| 4,160,978 A | 7/1979 | DuHamel | |
| 4,217,550 A | 8/1980 | Blassel et al. | |
| 4,260,990 A | 4/1981 | Lichtblau | |
| 4,375,289 A | 3/1983 | Schmall et al. | |
| 4,680,591 A | 7/1987 | Axford et al. | |
| 4,791,285 A | 12/1988 | Ohki | |
| 4,920,352 A | 4/1990 | Martensson et al. | |
| 4,977,614 A | 12/1990 | Kurcbart | |
| 5,128,686 A | 7/1992 | Tan et al. | |
| 5,206,592 A | 4/1993 | Buess et al. | |
| 5,221,902 A | 6/1993 | Jones et al. | |
| 5,227,725 A | 7/1993 | Cory et al. | |
| H1218 H | 8/1993 | Cory et al. | |
| 5,233,300 A | 8/1993 | Buess et al. | |
| 5,237,165 A | 8/1993 | Tingley, III | |
| 5,321,412 A | 6/1994 | Kopp et al. | |
| 5,459,451 A | 10/1995 | Crossfield et al. | |
| 5,513,383 A | 4/1996 | Tsao | |
| 5,572,226 A | 11/1996 | Tuttle | |
| 5,602,556 A | 2/1997 | Bowers | |
| 5,608,321 A | 3/1997 | Garroway et al. | |
| 5,804,967 A | 9/1998 | Miller et al. | |
| 5,817,207 A | 10/1998 | Leighton | |
| 5,903,242 A | 5/1999 | Tsuru et al. | |
| 5,914,692 A | 6/1999 | Bowers et al. | |
| 5,945,958 A | 8/1999 | Staufer et al. | |
| 6,031,508 A | 2/2000 | Ishizuka et al. | |
| 6,054,856 A | 4/2000 | Garroway et al. | |
| 6,147,605 A | 11/2000 | Vega et al. | |
| 6,194,898 B1 | 2/2001 | Magnuson et al. | |
| 6,195,006 B1 | 2/2001 | Bowers et al. | |
| 6,204,764 B1 | 3/2001 | Maloney | |
| 6,208,235 B1 | 3/2001 | Trontelj | |
| 6,208,874 B1 | 3/2001 | Rudisill et al. | |
| 6,281,794 B1 | 8/2001 | Duan et al. | |
| 6,411,208 B1 | 6/2002 | Buess et al. | |
| 6,420,872 B1 | 7/2002 | Garroway et al. | |
| 6,429,768 B1 | 8/2002 | Flick | |
| 6,522,135 B2 | 2/2003 | Miller et al. | |
| 6,535,175 B2 | 3/2003 | Brady et al. | |
| 6,597,318 B1 | 7/2003 | Parsche et al. | |
| 6,696,952 B2 | 2/2004 | Zirbes | |
| 6,777,937 B1 | 8/2004 | Miller et al. | |
| 6,814,284 B2 | 11/2004 | Ehlers et al. | |
| 6,825,754 B1 | 11/2004 | Rolin | |
| 6,900,633 B2 | 5/2005 | Sauer et al. | |
| 6,956,476 B2 | 10/2005 | Buess et al. | |
| 6,970,141 B2 | 11/2005 | Copeland et al. | |
| 6,989,750 B2 | 1/2006 | Shanks et al. | |
| 7,019,651 B2 | 3/2006 | Hall et al. | |
| 7,042,419 B2 | 5/2006 | Werner et al. | |
| 7,049,814 B2 | 5/2006 | Mann | |
| 7,064,668 B2 | 6/2006 | Porad | |
| 7,100,835 B2 | 9/2006 | Selker | |
| 7,132,942 B1 | 11/2006 | Buess et al. | |
| H2177 H | 1/2007 | Sauer et al. | |
| 7,215,293 B2 | 5/2007 | Chen et al. | |
| 7,330,161 B2 | 2/2008 | Matsugatani et al. | |
| RE40,145 E | 3/2008 | Leighton | |
| 7,375,639 B2 | 5/2008 | Dixon et al. | |
| 7,460,071 B2 | 12/2008 | Manholm et al. | |
| 7,591,415 B2 | 9/2009 | Jesme | |
| 7,612,675 B2 | 11/2009 | Miller et al. | |
| 7,612,676 B2 | 11/2009 | Yuen et al. | |
| 7,714,724 B2 | 5/2010 | Halope et al. | |
| 7,714,791 B2 | 5/2010 | Lavedas | |
| 7,808,389 B2 | 10/2010 | Finkenzeller | |
| 8,098,161 B2 | 1/2012 | Lavedas | |
| 8,674,697 B2 | 3/2014 | Apostolos et al. | |
| 8,717,242 B2 | 5/2014 | Lavedas et al. | |
| 2003/0146839 A1 | 8/2003 | Ehlers et al. | |
| 2003/0197653 A1 | 10/2003 | Barber et al. | |
| 2004/0006424 A1 | 1/2004 | Joyce et al. | |
| 2004/0207527 A1 | 10/2004 | Shanks et al. | |
| 2005/0093677 A1 | 5/2005 | Forster et al. | |
| 2005/0093678 A1 | 5/2005 | Forster et al. | |
| 2005/0179604 A1* | 8/2005 | Liu | H01Q 1/2225 343/742 |
| 2005/0212673 A1 | 9/2005 | Forster | |
| 2007/0185546 A1 | 8/2007 | Tseng et al. | |
| 2008/0231458 A1 | 9/2008 | Fein | |
| 2008/0238684 A1 | 10/2008 | Tuttle | |
| 2009/0021343 A1 | 1/2009 | Sinha | |
| 2010/0001080 A1 | 1/2010 | Sim et al. | |
| 2010/0001914 A1 | 1/2010 | Lavedas | |
| 2010/0069011 A1 | 3/2010 | Carrick et al. | |
| 2010/0134291 A1 | 6/2010 | Lavedas | |
| 2012/0206238 A1 | 8/2012 | Lavedas | |
| 2012/0206309 A1 | 8/2012 | Lavedas et al. | |
| 2013/0307740 A1* | 11/2013 | Pajona | H01Q 7/00 343/748 |
| 2014/0070810 A1 | 3/2014 | Robert et al. | |
| 2014/0118116 A1 | 5/2014 | Lavedas | |
| 2015/0009088 A1 | 1/2015 | Lavedas | |

OTHER PUBLICATIONS

PCT International Preliminary Report on Patentability of the ISA dated Jan. 5, 2011 for PCT Patent App. No. PCT/US2009/049136; 8 pages.

Notification of Transmittal of the International Search Report and the Written Opinion of the International Searching Authority, or the Declaration, PCT/US2009/049136, dated Aug. 4, 2009, 12 pages.

Abedin, M.F., A Low Profile Dipole Antenna Backed by A Planar EBG Structure, Department of Electrical Engineering, 2006, pp. 13-16 U.of S.C.

Analog Devices, MT-095 Tutorial; "EMI, RFI, and Shielding Concepts", Rev.0, Jan. 2009, WK, pp. 1-16.

Apostolopoulos et al., Electromagnetic Band Gap Characteristics From Closely Coupled Double Layer and Dipole and Tripole Arrays, 2003, The Institute of Electrical Engineers, pp. 409-412.

Azcona et al., "Micromachined Electromagnetic Bandgap Crystals as Antenna Substrates for a 500 GHz Imaging Array", pp. 1-7.

Clavijo et al., Design Methodology for Sievenpiper High-Impedance Surfaces: An Artificial Magnetic Conductor for Positive Gain Electrically Small Antennas, 2003, pp. 2678-2690, IEEE Antennas and Wireless Propagation, vol. 51, No. 10.

Design & System Integration Division Defense & Security, Scientific Report 2008, Cea Leti; Savry et al., "Secure RFID transactions with a noisy reader," p. 9.

Kurs et al.; "Wireless Power Transfer via Strongly Coupled Magnetic Resonances;" www.sciencemag.org; vol. 317, dated Jul. 6, 2007; pp. 83-86.

Mardev Asia, May 1, 2006, Symbol Technologies Launches Portfolio of RFID Inlays and Trays, 1 page.

Sievenpiper et al., High-Impedance Electromagnetic Surfaces With a Forbidden Frequency Band, 1999, pp. 2059-2074, IEEE Transactions on Microwave Theory and Techbiques, vol. 47, No. 11.

Symbol Technologies Launches Portfolio of RFID Gen 2 and Specialty Tag Inlays, May 1, 2006, pp. 1-2.

Two RF Inputs Make a Better RFID Tag, May 2006, Symbol the Enterprise Mobility Company, pp. 1-4.

Ukkonen et al., Effects of Metallic Plate Size on the Performance of Microstrip Patch Type Tag Antennas for Passive RFID, 2005, pp. 410-413, IEEF Antennas and Wireless Propagation Letters, vol. 4.

Whites et al., "Easily Designed and Constructed High Impedance Surfaces", Department of Electrical and Computer Engineering, 2003, pp. 407-410, South Dakota School of Mines and Technology, Rapid City, SD.

Zetter, K. "Jamming Tags Block RFID Scanners", wired magazine online, Mar. 1, 2004, 4 pages, http://www.wired.com/techbiz/media/news/2004/03/62468?currentPage=all, last accessed Feb. 28, 2011.

* cited by examiner

PRIOR ART

NEAR-FIELD GRADIENT PROBE FOR THE SUPPRESSION OF RADIO INTERFERENCE

CROSS REFERENCE TO RELATED APPLICATION

The present application claims priority to a provisional application having Ser. No. 62/015,679, entitled "Improved Near-Field Gradient Probe for the Suppression of Radio Interference," filed on Jun. 23, 2014, Inventor Thomas G. Lavedas, which is hereby incorporated by reference.

FIELD

At least some embodiments described herein may relate to RF circuits, probe structures, antenna systems, and related techniques and methods to improve undesirable far-field suppression and intra-probe isolation in part or all of these devices, using electrically adaptive structures, methods, and techniques, as well as systems, methods, and devices for improving near-field sensing applications, like RFID and explosive detection systems.

BACKGROUND

Antenna systems have near-field and far-field radiation regions. The near field is a region near an antenna where the angular field distribution depends upon the distance from the antenna. The near field is generally within a small number of wavelengths from the antenna and is characterized by a high concentration of energy and energy storage in non-radiating fields. In contrast, the far field is the region outside the near field, where the angular distributions of the fields are essentially independent of the distance from the antenna. Generally, the far-field region is established at a distance of greater than $D^2/\lambda$ from the antenna, where D is an overall dimension of the antenna that is large compared to wavelength $\lambda$. The far-field region is where radiation from the antenna is said to occur.

Some Radio Frequency Identification (RFID) systems, for example, use near fields for communications between the RFID tag and the RFID interrogator, and the energy stored in the near fields provides the power to drive a microchip imbedded in a passive RFID transponder tag. RFID systems are typically wireless, non-contact systems that use radio frequency electromagnetic fields to transfer information from an RFID card or tag to a reader for the purposes of automatic identification and/or tracking. Antennas used to create and exploit the energy in their near-field are found useful in RFID, nuclear magnetic resonance (NMR), quadrupole resonance (QR) and other applications. Used in this manner, these antennas may commonly be referred to as sensor probes.

At least some known RFID and some explosive detection systems use loop-type radiators for interrogator antennas, for example, an antenna consisting of a figure-eight shaped conductor to effect a reduction in the creation or reception of energy in their far-field regions. That is, loop antenna systems can be designed such that the coupling between the antenna and its nearby surroundings is relatively high, whereas the coupling between the antenna and its distant surroundings is minimized. By using two or more loops in combination, where the loops have a specific size and geometry, the magnitude of the current within the loops and the direction of the currents generated fields work to cancel each other out in the far-field region (that is, the sum of the fields created from each of the antenna loops is close to zero.)

One application for near field probes (including those using loop-type radiators) is in a detection system used to exploit a material's Nuclear Quadrupole Resonance (NQR), where NQR is a radio frequency (RF) magnetic spectroscopic technique that has been used to create a system to detect and identify a wide range of materials based on detection of the resonances associated with their quadrupolar nuclei. The NQR response signal provides a unique signature of the material of interest, where the detected electrical signal indicates the presence of quadrupolar nuclei. Exemplary uses for NQR include (but are not limited to), screening of airline baggage, parcel screening, detection of drugs/narcotics, and detection of explosives, such as detection of buried Improvised Explosives Devices (IED), and/or landmine detection. The particulars of the operation of several exemplary NQR detection systems are discussed in U.S. Pat. Nos. 6,777,937, 6,194,898, and 7,049,814, each of which is hereby incorporated by reference in its entirety.

SUMMARY

One issue, however, with systems that use near-field probes and related technologies, especially for detection and screening of explosives, is suppression of RF interference (RFI). Suppression of RFI is particularly relevant for NQR systems, which rely on detection of a relatively weak or small signal (NQR signals inherently can be very weak). Detection of NQR signals, using near-field probe (antenna) systems such as loop antennas, can be difficult in the presence of strong far field noise sources/signals, such as AM radio transmitters, and nearby noise sources/signals, such as automobile ignitions, computers, mobile phones, and other electronics. Note that, the region outside of the very near vicinity of the near-field probe embodiments discussed herein is still technically part of the near-field, but, for at least some embodiments disclosed further herein, is outside of the most sensitive region of at least some of the antenna systems/probes described herein. Therefore, these "technically" near field signals are effectively, in some embodiments described further herein, suppressed, though not as fully suppressed as are the signals that are emanating from the far-field region.

The presence of strong far field noise sources/signals presents a difficulty that arises at least in part because these kinds of noise sources can create substantial coherent and non-coherent geographically distributed noise that can be within the detection frequency ranges of interest. For example, detection of land mine explosives such as tri-nitrotoluene (TNT) can be affected by amplitude modulation (AM) radio signals sourced in the far field, because the characteristic detectable frequencies associated with TNT (used in NQR detection systems) are below 1 MHz, which is within in the standard AM radio band.

The following presents a simplified summary in order to provide a basic understanding of one or more aspects of the embodiments described herein. This summary is not an extensive overview of all of the possible embodiments, and is neither intended to identify key or critical elements of the embodiments, nor to delineate the scope thereof. Rather, the primary purpose of the summary is to present some concepts of the embodiments described herein in a simplified form as a prelude to the more detailed description that is presented later.

It is desirable to suppress RFI emanating from distant sources, so that this RFI does not interfere with detection of the desired signal. Some known implementations that attempt to suppress RFI use a single sensor probe configuration to implement both transmit and receive functions augmented with a remote RFI sampling antenna coupled to a weighted feedback loop to reduce susceptibility to RFI. These kinds of implementations can introduce undesirable performance compromises that can lead to performance degradations. In particular, the desire to maximize the efficiency of the receive function works in opposition to the desire to limit the time it takes for the transmit energy in the probe to dissipate after the transmit pulse is ended. Still other implementations may incorporate shielding over some or all of the probe in an attempt to reduce RFI interference; this is more common with larger resonant probes, and can result in bulky probe configurations. Further, such shielding is best suited for detection of buried threats, but is much less effective in personnel screening applications.

At least some other known techniques for suppressing RFI, especially with loop antennas and systems/probes that incorporate loop antennas, have relied on active cancellation using remote sense antennas (i.e., monitoring the RFI with a separate antenna and then subtracting the unwanted RFI signal(s). The use of remotely located sampling antennas can limit the effectiveness of this approach because the distributed nature of the RFI cause signals acquired from a different location to vary significantly is ways that cannot be fully compensated for by adjusting the phase and amplitude of the acquired sample. Use of remote sampling antennas also can impose stringent linearity requirements on the active components of the system, that is, the first stage of amplification (e.g., the low-noise amplifier (LNA)).

In one embodiment described herein, an approach is provided to help improve RFI suppression, where the approach relies at least in part on using a probe (also referred to herein as an antenna system, antenna probe system, or near-field probe) formed by loops of conductors, which uses the geometry of the probe to passively suppress the reception of the RFI emanating from distant sources. This approach uses a unique geometry that can help to maximize the rejection of the RFI. For example, in one aspect, a probe is described herein that has a specific geometric ratio between three loops of conductors, two of which are connected together in electrical opposition in such a manner as to eliminate the magnetic coupling between this pair of loops and the third loop. In one embodiment, the loops of conductors are not "closed" loops; rather, they are open at an appropriate point to form an output/input feed point (also referred to herein as a balanced feed point, balanced port, or feed port) such that they can be interconnected with the other loops or connected to their respective tune/match circuitry.

The two components thus created are individually tuned and impedance matched in such a way as to allow their summed electrical response to be substantially or even completely devoid of the unwanted RF interference component of the energy impinging on the total sensor system thus created. Further, electronically controlled components are introduced that permit the amplitude and phase of one of the components to be automatically and independently adjusted to maximize the RFI rejection, in a substantially automatic manner, to compensate substantially or even completely, for at least some anomalies present in the physical dimensions of the sensor geometry and the probes immediate surroundings. This automatic adjustment can be used independent of, or in connection with, mechanical adjustment of some or all of the antenna system components, to help ensure substantially accurate and precise adjustment of the probe.

It is believed that no such previous automatic compensation system, whether alone or used in connection/cooperation with mechanical systems, is known to exist in the current state-of-the-art. In particular, at least some of the described embodiments provide a unique and useful antenna system/probe configuration that includes a precise assembly of loops to create two independent, collocated antennas that can then be combined under automated control. At least some of the described embodiments provide advantages and features not seen in known loop antenna configurations or in systems used for automated tuning of antennas.

In addition, in a further aspect, an optimum geometric relationship is provided between a fourth conductor loop, dedicated to the transmit function, such that the receive and transmit portions of the complete sensor system can be operated independently from one another.

In one embodiment, an apparatus is provided having a geometry of three loops that rejects RFI from far-field sources and permits the automatic adjustment for the purpose of optimizing the RFI rejection performance.

In another embodiment, an apparatus is provided that provides automatic adjustment of the phase and amplitude of one component of the complete sensor system such that the sum response of the two parts contains a minimum interference related response.

In yet another embodiment, an apparatus is provided having a fourth loop, where the geometry of the fourth loop isolates it from the sum of the three loops), such that the fourth loop may be placed coplanar with sum of the first three loops (or inner loops) and operated independently from it. In still further embodiments, more than two inner loops can be summed together, and used with a separate loop having a geometry enabling it to be isolated from the sum of the inner loops, to create far field suppression.

Improving the RFI suppression and/or automatically adjusting loop geometry and/or electrical performance, as described herein, also may advantageously, in at least some embodiments, increase the operating range of the systems into which such loop antenna systems are placed.

In one embodiment, an antenna system is provided comprising first, second, and third loop antennas. The first loop antenna comprises a first conductor forming a first loop, the first loop having a first respective loop area. The second loop antenna is spaced apart from the first loop antenna, the second loop antenna comprising a second conductor forming a second loop, the second loop antenna having a second respective loop area. The third loop antenna is spaced apart from both the first and second loop antennas, the third loop antenna comprising a third conductor forming a third loop. The first and third loop antennas are operably coupled together in electrical opposition to each other, configured to be driven to form a first independent balanced feed point, and configured to be substantially electrically and magnetically isolated from the second loop antenna. The second loop antenna is configured to be driven from a second balanced feed point. The first, second and third loops are configured such that a sum of the first and second respective loop areas, at a sum port in operable communication with the first and second balanced feed points, is substantially equivalent, within a predetermined tolerance, to the third respective loop area. The first and second balanced feed points are in operable communication with an automatic control system configured to automatically and independently adjust at least one of amplitude and phase for at least one of the first, second, and third loops in operable communication with at least one of the first and second balanced feed points, where each respective automatic and independent adjustment is configured to help to substantially maximize suppression of RFI for a sum of signals from the first and second balanced feed points.

In another embodiment, the automatic control system comprises first amplitude and phase adjustment circuits. The first amplitude adjustment circuit is in operable communication with the automatic control and a respective one of the first and second loops. The first phase adjustment circuit in operable communication with the automatic control and a respective one of the first and second loops. The first amplitude adjustment circuit is configured to operate independently of the first phase adjustment circuit.

In another embodiment, the automatic control system further comprises a first tune/match adjustment circuit in operable communication with the automatic control and a respective one of the first and second loops, the tune/match adjustment circuit configured to provide coarse tuning of the respective one of the first and second loops.

In yet another embodiment, the automatic control system further comprises a first tune/match adjustment circuit in operable communication with the automatic control and a respective one of the first and second loops, the tune/match adjustment circuit configured to provide phase matching for the respective one of the first and second loops.

In a still further embodiment, the antenna system is in operable communication with a mechanical control configured to adjust a size of one of the first, second, and third loops, wherein the adjustment(s) provide by the mechanical control cooperate with one or more of the adjustments performed by the automatic control, to help to substantially maximize suppression of RFI.

In another embodiment, the first loop comprises an inner loop, the second loop comprises a middle loop, and the third loop comprises an outer loop. In a further aspect of this embodiment, for a given inter-loop ratio factor K, the inter-loop ratios are defined as follows:

$$K_{(outer\ loop)} = 1$$

$$K_{(middle\ loop)} = \sqrt{\frac{K}{2}}$$

$$K_{(inner\ loop)} = \sqrt{\left[\frac{2-K}{2}\right]}$$

In still another aspect of this embodiment, K is between about 1.125 to about 1.25.

In a further embodiment, at least two of the first, second, and third loops of the antenna system have substantially similar shapes. In another embodiment, at least two of the first, second, and third loops are substantially concentric. In another embodiment, at least one of the first, second, and third loops comprises a respective set of two or more sub-loops, each sub-loop having a respective sub-loop area, wherein the sum of all the respective sub loop areas in the respective set is substantially equivalent to the respective loop area of the at least one of the first, second and third loops. In another embodiment, the first, second and third loops are substantially coplanar. In yet another embodiment, the first and third loops are substantially coplanar and lie within a first plane, and the second loop lies within a second plane that is spaced apart from but parallel to the first plane.

In a still further embodiment:

(a) if any two of the first, second, and third loops have substantially the same respective loop area as each other, then a first spacing S1 is defined as being between the two loops having substantially the same respective loop area; and (b) if the respective loop areas of any two of the first, second and third loops, when added together, form a pair of loops that together have substantially the same loop area as the remaining one of the first, second and third loops, then a second spacing S2 is defined as being between either one of the pair of loops and the remaining one of the first, second, and third loops;

wherein at least one of S1 and S2 is selected to help to maximize RFI suppression at a given operational frequency $\lambda$. where:

$$RFI\ Suppression = 2\sin\left(\frac{\pi S}{\lambda}\right).$$

In still another embodiment, the antenna system comprises a fourth loop antenna spaced apart from the first, second, and third loop antennas, wherein the first, second, third and fourth the fourth loop antennas are substantially concentric and coplanar, wherein the fourth antenna comprises a fourth conductor forming a fourth loop that is configured to be substantially electrically and magnetically isolated from the first, second, and third loop antennas, wherein the fourth loop is configured to include a third balanced feed point that is electrically independent of the sum port of the first, second, and third loops; wherein the first, second, and third loop antennas are configured to instantiate a selected one of a transmit and a receive function; and wherein the fourth loop antennas is configured to instantiate the other of the transmit and receive functions, such that the fourth loop antenna performs a different function than the first, second, and third loop antennas.

In another aspect, a method of increasing suppression of RFI in an antenna system comprising first, second, and third loops, is provided. The first, second, and third loops are sized such that a sum of an area defined by the inner loop and an area defined by the second loop is substantially equivalent, within a predetermined tolerance, to an area defined by the third loop. The first and third loops are operably coupled together in electrical opposition to each other. The first and third loops are configured to be driven from a first independent balanced feed point and to be substantially electrically and magnetically isolated from the middle loop. The second loop is configured to be driven from a second balanced feed point. At least one of amplitude and phase is automatically and independently adjusted for at least one of the first, second, and third loops in operable communication with at least one of the first and second balanced feed points, where each respective automatic and independent adjustment is configured to help to substantially maximize suppression of RFI for a sum of signals from the first and second balanced feed points.

In a further embodiment, for a given inter-loop ratio factor K, the inter-loop ratios are defined as follows:

$$K_{(third\ loop)} = 1$$

$$K_{(second\ loop)} = \sqrt{\frac{K}{2}}$$

$$K_{(first\ loop)} = \sqrt{\left[\frac{2-K}{2}\right]}$$

In a further embodiment, K is between about 1.125 to about 1.25.

In yet another embodiment, a fourth loop antenna is provided, where the fourth loop antenna is spaced apart from the first, second, and third loop antennas, wherein the first, second, third and fourth the fourth loop antennas are substantially concentric and coplanar, wherein the fourth antenna comprises a fourth conductor forming a fourth loop that is configured to be substantially electrically and magnetically isolated from the first, second, and third loop antennas, wherein the fourth loop is configured to include a third balanced feed point that is electrically independent of the sum port of the first, second, and third loops. The first, second, and third loop antennas are configured to instantiate a selected one of a transmit and a receive function. The fourth loop antenna is configured to instantiate the other of the transmit and receive functions, such that the fourth loop antenna performs a different function than the first, second, and third loop antennas.

In another embodiment, the antenna system is operably coupled to a controller, the controller comprising at least one of an automatic electronic control and a mechanical control, wherein the controller is configured to cooperate with the automatic control system to adjust at least one of the following to help maximize suppression of RFI:

(a) a size of one of the first, second and third loops;
(b) a phase of one or both of the first and second loops;
(c) an amplitude of one or both of the first and second loops;
(d) a coarse tune of one of the first and second loops
(e) a phase match for one of the first and second loops
(f) a coarse tune of a respective one of the first and second loops; and
(g) a spacing between any two of the first, second, and third loops.

Details relating to these and other embodiments are described more fully herein.

BRIEF DESCRIPTION OF THE DRAWINGS

The advantages and aspects of the described embodiments will be more fully understood in conjunction with the following detailed description and accompanying drawings, in which.

The drawings are not to scale, emphasis instead being on illustrating the principles and features of the disclosed embodiments. In addition, in the drawings, like reference numbers indicate like elements.

DETAILED DESCRIPTION

Figure 1:
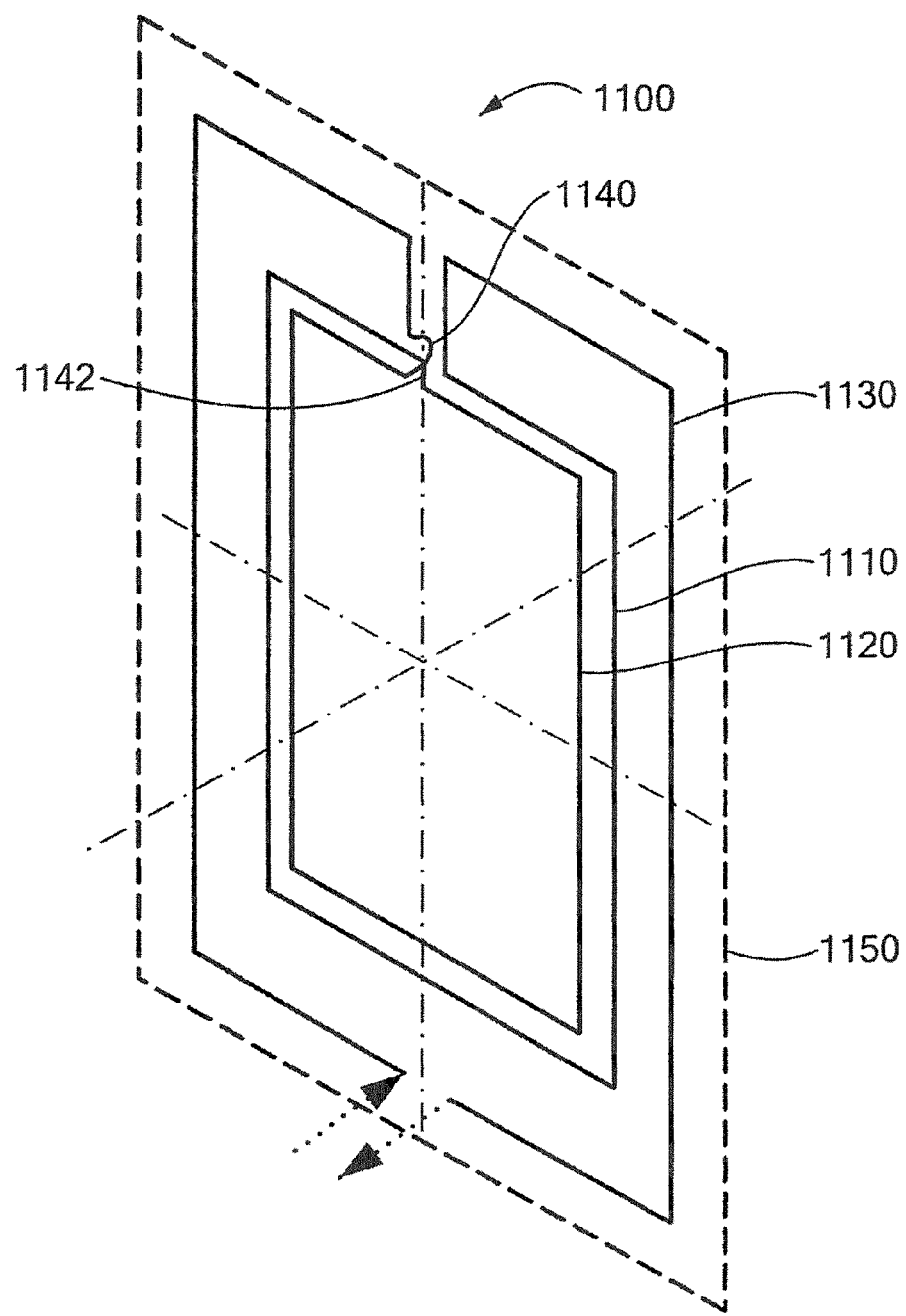
FIG. 1 illustrates an antenna configuration of loops as known in the prior art.

The following detailed description is provided, in at least some examples using the specific context of specific types of near-field radio frequency (RF) communications systems. For example, at least some embodiments herein are usable with near-field RF communications systems adapted for use as part of a radio-frequency identification (RFID) system and/or are usable with or as part of nuclear quadrupole resonance (NQR) systems. It should be appreciated that such references and examples are made in an effort to promote clarity in the description of the concepts disclosed herein. Such references are not intended as, and should not be construed as, limiting the use or application of the concepts, systems, circuits, and techniques described herein to use solely with RFID and/or NQR systems. In addition, although many of the exemplary embodiments are described in connection with suppression of RFI energy being received (e.g., RFI on far field reception), these embodiment are equally applicably to suppression of far field energy on transmission (radiation) as well, as will be appreciated. At least some of the exemplary embodiments are further applicable to systems capable of receiving and transmitting at the same time, thus substantially suppressing RFI energy received as well as far field energy on transmission.

The systems, methods, and apparatuses described herein are anticipated to be usable with many different types of systems, and at least some of the embodiments described herein are applicable to any devices that incorporate loop antennas or that requires precise adjustment of loop antennas, including but not limited to probes, such as near field probes. Furthermore, the concepts, systems, circuits and techniques described herein may find application in a wide variety of different types of transponder systems and other RF systems. Such systems include, but are not limited to proximity readers, near-field sensing systems, metal detectors, shortwave transceivers, and concealed or covert communications applications. Accordingly, it will be appreciated that the concepts, circuits and techniques described herein within the context of an RFID system could equally be taking place in other types of RF communication and/or transponder systems or networks, without limitation.

As used herein a "loop antenna" configuration may comprise two (i.e., a pair) or more than two loop antennas. That is, reference made herein to a single loop (e.g., a first loop) may in fact be referring, in at least some embodiments, to a set of sub-loops that together are treated as a single loop, especially if the sum of the respective loop areas of the sub-loops is equivalent to that of the single loop. A loop antenna system (or more simply an "antenna system") may include multiple loop antenna sets (for example, multiple sets of two or more loop antennas for use in RFID and other systems). As noted previously, any of the loop antenna systems or configurations described herein can be used as part of a probe, such as a near field probe or near field gradient probe, as will be appreciated.

Also, reference is sometimes made herein to a loop antenna system having a particular number of loops. It should of course, be appreciated that a loop antenna system may be comprised of any number of loops and that selection of the particular number of loops to use in any particular application is based on a number of known factors. In addition, reference is sometimes made herein, both in the text and in the drawings, to a loop antenna system having a particular shape or physical size. It will be appreciated that the concepts and techniques described herein are applicable to various sizes and shapes of loops and/or arrays, that any number of loop antenna elements may be used, and that how to select the particular sizes, shapes of number of loops to use in any particular application is based on some known factors.

Similarly, reference is sometimes made herein to a loop antenna having a particular geometric shape (e.g. square, rectangular, triangular, round, octagonal, polygonal) and/or size (e.g., a particular number of loop antenna elements) or a particular spacing or arrangement of loop antenna elements. It will be appreciated that the techniques described herein are applicable to various sizes and shapes of loop antennas. Further, for a given configuration of loop antennas, it is not necessary for all the antennas to have the same shape.

Thus, although the description provided herein below describes the inventive concepts in the context of one or more particular illustrated and/or described loop antenna systems, it will be appreciated that the concepts equally apply to other configurations, sizes and shapes of loop antennas.

Also the concepts described herein in the context of loop antenna elements may find use in antenna elements implemented in a variety of manners including implemented as any type of printed circuit antenna or wire or tubular conductor loop antenna (regardless of whether the element is a printed circuit element) known in the art.

The inventor of the present application is a listed inventor on U.S. Pat. No. 7,714,791, entitled "Antenna with improved illumination efficiency" (hereinafter "791 patent"), which patent is hereby incorporated by reference in its entirety. Several antenna configurations applicable to RFID and wireless electric power transmission that have favorable characteristics are described in the '791 patent. In addition, the '791 patent includes, among its described embodiments, an antenna concept for near field sensor applications. The configuration illustrated in prior art FIG. 1 herein (which corresponds substantially to FIG. 11A of the '971 patent) proved to be of particular interest and utility.

FIG. 1 shows an embodiment of a prior art antenna 1100 similar to that shown in the '971 patent, which antenna 1100 can be substantially flat and disposed a plane designated by reference numeral 1150. The antenna 1100 includes first loop 1110, a second loop 1120, and a third loop 1130 which are substantially coplanar in plane 1150. A coupler element 1140 supplies a current from the third loop 1130 to one of the first and second loops 1110, 1120. In the configuration shown in FIG. 1, the coupler element 1140 juts out a distance from the plane 1150 in order to couple the third loop 1130 to the second loop 1120. An inner loop element 1142, disposed in plane 1150, couples the first and second loops 1110, 1120. The current flows in a first polarity through the third loop 1130, and in a second polarity opposite to the first polarity in first and second loops 1110, 1120. The loops 1110, 1120, and 1130 may be disposed on a single side of an insulating material, such as a printed circuit panel, for ease of fabrication.

Referring still to FIG. 1 (and to the associated discussions of FIGS. 9 and 11A of the referenced '791 patent), with this configuration, characterized by an outer loop 1130 surrounding inner loops 1120 and 1120, the outer loop 1130 having an outer loop enclosed area equal in size to the sum of each of the inner loop enclosed areas, the far-field radiation is cancelled to a high degree, while the near-field energy is not as substantially impacted. In the referenced '791 patent, far-field radiation cancellation is dependent on the inner loops 1110 and 1120 having substantially equal enclosed areas. The inner loops produce a substantially higher near-field energy peak along an axis coincident to the inner loops. Thus, the reduction in the near-field energy is not complete. Rather, a usable level of near-field energy can be produced at greater distances from the antenna 1100 while maintaining radiation levels low enough to satisfy prevailing governmental RF radiation regulations.

In addition to the aforementioned '791 patent, the inventor of the present application also is a named inventor on U.S. Pat. No. 8,717,242 ("'242 patent"), entitled "Method for Controlling Far Field Radiation from an Antenna," which patent is also hereby incorporated by reference in its entirety. The '242 patent includes at least some embodiments that describe means of reducing losses and compensating for manufacturing tolerances needed to assure the highest level of performance. In addition, at least some embodiments of the '242 patent improve at least some of the technology described in the '791 patent. The concepts described herein also may find applicability in combination with either or both of the '242 and '791 patents as well as some or all of the disclosure contained in U.S. Patent Publication No. 20150009088, entitled "Diplexing and Triplexing of Loop Antennas" (hereinafter "088 application"), listed inventor Thomas Lavedas, filed on Jul. 8, 2013, published on Jan. 8, 2015, which patent application is hereby incorporated by reference.

The aforementioned '791 patent dealt with the use of the antenna in a transmitting mode of operation, in particular within an RFID interrogator or in a wireless transmission of electric power application. In that role, one goal that resulted was to minimize the far-field radiation component of the fields being created. However, as shown in at least some of the embodiments described herein, an antenna similar to the antenna of FIG. 1 can be precisely modified, adapted, and controlled, as described herein, into a new apparatus configured to reject the reception of interfering signals generated at distances associated with the far field region around the antenna, while maintaining reception of the signals generated in the near vicinity (e.g., the near field). Further, at least some of the embodiments described herein apply modified implementations of some of the concepts of the aforementioned '791 patent to near-field sensing applications, using an antenna based on the antenna of FIG. 1, but further modified and substantially and precisely adapted and controlled as described further in this application, to achieve advantages that include rejection of interfering signals generated at distances associated with the far-field region around the antenna, while maintaining reception of the signals generated in the near vicinity. For example, in one embodiment disclosed herein, improved RFI suppression is possible for interfering signals that appear or are generated at a distance that is 10-15 times the diameter of the antenna (or loop antenna) that is sensing the interfering signals. In a further embodiment, the modified antenna provides a relative suppression that begins at about one-half of the diameter of the loop antenna, where the suppression is taken conceptually to be a loss out to a diameter or two. In one embodiment, the reception of a signal originating at that distance is reduced by a factor of about 30 relative to that received by a conventional loop. In a further embodiment, a signal originating 10-15 diameters or more from the subject gradiometer is suppressed by a factor significantly greater than 30, substantially equal to the maximum that is practically achievable In particular, the present inventor has recognized that the concepts, apparatuses, methods, and systems initially presented in his prior '791 and '242 patents can be modified, changed, and expanded further (as described in accordance with at least some of the embodiments described herein) and applied to the other problems, such as the problem of detecting explosive materials using the phenomena of nuclear quadrupole resonance (NQR). At least some known NQR systems have demonstrated the ability to determine the exact composition of materials by their RF spectral responses. But, the performance of these known NQR systems can be severely degraded by radio frequency interference (RFI) when removed from the laboratory and applied in at least some real-world applications, such as land mine detectors.

Experiments with the modified versions of the antenna of FIG. 1, as well as with other designs described in connection with FIGS. 2-8 herein, have demonstrated RFI suppression in excess of 50 dB (100,000:1), thereby offering the potential to build larger and more sensitive detection systems than have previously been considered practical. In addition, in at least some embodiments, the RFI suppression resulting from the configurations described herein may even be usable to help suppress at least some unwanted signals arising in regions other than the far field region, such as jamming types of signals arising either in the near field region or in a region in between the near and far field regions.

Because systems such as the aforementioned detection systems often require a significant level of noise suppression, it is advantageous, in at least some disclosed embodiments, for the loop geometry to be very exact. Consequently, a way to precisely adjust for inaccuracies in the loop geometry or the effects of the immediate surroundings is very desirable. It is further desirable for this adjustment to be automatic.

In the aforementioned '242 patent, at least some disclosed embodiments proposed several ways to make allowances for variations in loop geometry using purely mechanical means. With at least some embodiments described in the present application, however, the inventor has developed at least some embodiments providing a means of providing improved tolerance control using automated electronic means in addition to or in place of the mechanical adjustments of his '242 patent. The automated control and adjustments described for at least some embodiments described herein offer precision and improved performance that appear not to be possible in previously known systems. Furthermore, at least some of the automated tolerance control embodiments described herein have applicability to many other types of antenna systems and other circuits, as will be appreciated.

The subject RFI suppression of the present disclosure is at least partially predicated on summing the responses from two electrically opposing parts of a set of conductive loops. In particular, one larger loop is electrically opposed by the sum of the response derived from two or more smaller loops whose aggregate area is exactly equal to that of the larger loop. The smaller loops are, in at least some embodiments, centered in substantially or exactly the same plane as the larger loop so as to collect as nearly identical a sample of the incident energy as is possible.

As noted above, one solution to the problem of assuring the highest possible level of RFI suppression, as described at least partially in the '791 and the '242 patents, is to introduce mechanical adjustments into one of the antenna loops so as to permit the matching of the smaller and larger loop areas. However, in at least some embodiments, this approach is better suited for a one-time calibration, or at best requires the addition of bulky motors or actuators to implement the adjustments in an automated fashion. In contrast, providing an electronic control mechanism, whether alone or in combination with mechanical and/or electromechanical approaches, as described in connection with at least some of the embodiments disclosed herein, helps to permit faster, near-real-time adjustments to be made. In addition, at least some of the embodiments disclosed herein provide an approach that is also capable of applying a phase adjustment independent to the amplitude adjustment, which the previously described mechanical solution was incapable of doing.

Figure 2:
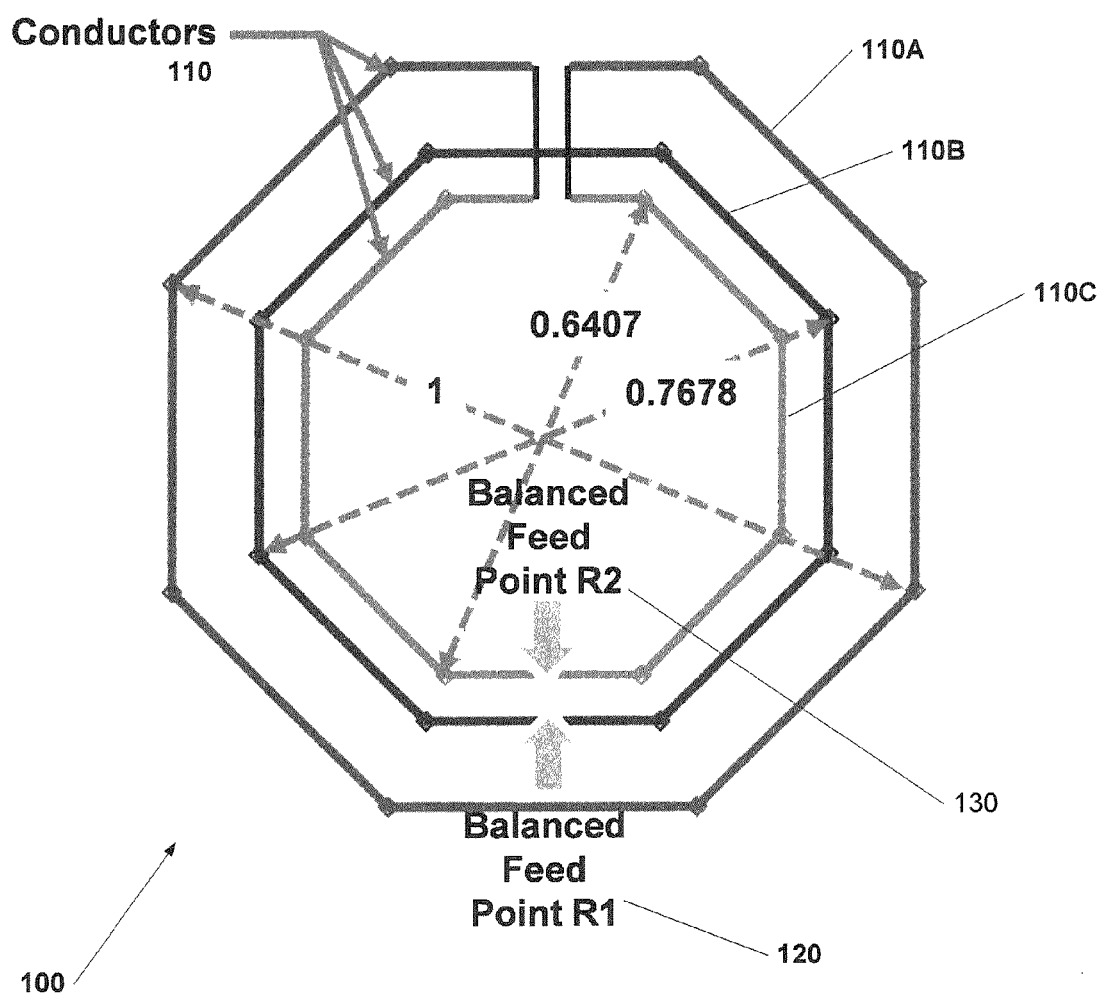
FIG. 2 illustrates an exemplary geometric relationship of three loops, in accordance with one embodiment.

Implementation of an electronic adjustment mechanism is achieved, in one embodiment, at least in part by applying a unique geometric relationship between a set of three or more conductor loops such that one or more of the loops is magnetically isolated from the remaining loops. One such geometric relationship for a set of three (first, second, and third) octagonal loops is illustrated in FIG. 2, which illustrates an exemplary geometric relationship 100, of three loops of conductors 110, in accordance with one disclosed embodiment (the octagonal shape is, of course, illustrative and not limiting). Referring to FIG. 2, the arrangement includes an outer loop 110A (third loop), a middle loop 110B (second loop), and an inner loop 110C (first loop), as well as a first balanced feed point (port R1) 120 and a second balanced feed point (port R2) 130. In this configuration, although the outer loop 110A, middle loop 110B, and inner loop 110C are substantially coplanar, there is electrical isolation between the first and second balanced feed points 120, 130, respectively.

In an alternate embodiment (not shown), the inner loop 110A could instead be made of two or more smaller loops that, in total, have a substantially or exactly equivalent area to that of the inner loop 110A. As will be appreciated, in an alternate embodiment, a different loop, such as the middle loop 110 or outer loop 110c, could instead be made of two or more smaller loops that, in total, have substantially or exactly an equivalent area to that of the respective middle loop 110b or outer loop 110c, but this might increase mechanical complications significantly, and ratios of loop sizes may change from those described for other embodiments herein. In addition, replacing any one of the loops with multiple smaller loops might change ratios between loop sizes.

Although the ratios discussed herein can vary (that is, the ratios discussed herein e.g., the inter-loop ratio factors, etc.), this geometry of FIG. 2 still results in a configuration that helps to maximize the isolation between loops (and, hence, improve the RFI suppression), because the middle loop 110B is still, effectively, an isolated port (i.e., port R1). In further embodiments, it is possible to have other combinations of loops, where individual loops can be replaced by smaller sets of loops, so long as the ratios are satisfied and/or the substantially equivalent area relationships are maintained. However, as one of skill in the art will appreciate, adding more conductors may result in more loss and does not necessarily provide any performance, isolation, or RFI suppression gains. In at least some embodiments, to compensate for possible losses that arise from adding conductors, it may be possible to increase the efficiency by increasing the size of the conductors forming the loops.

Figure 7:
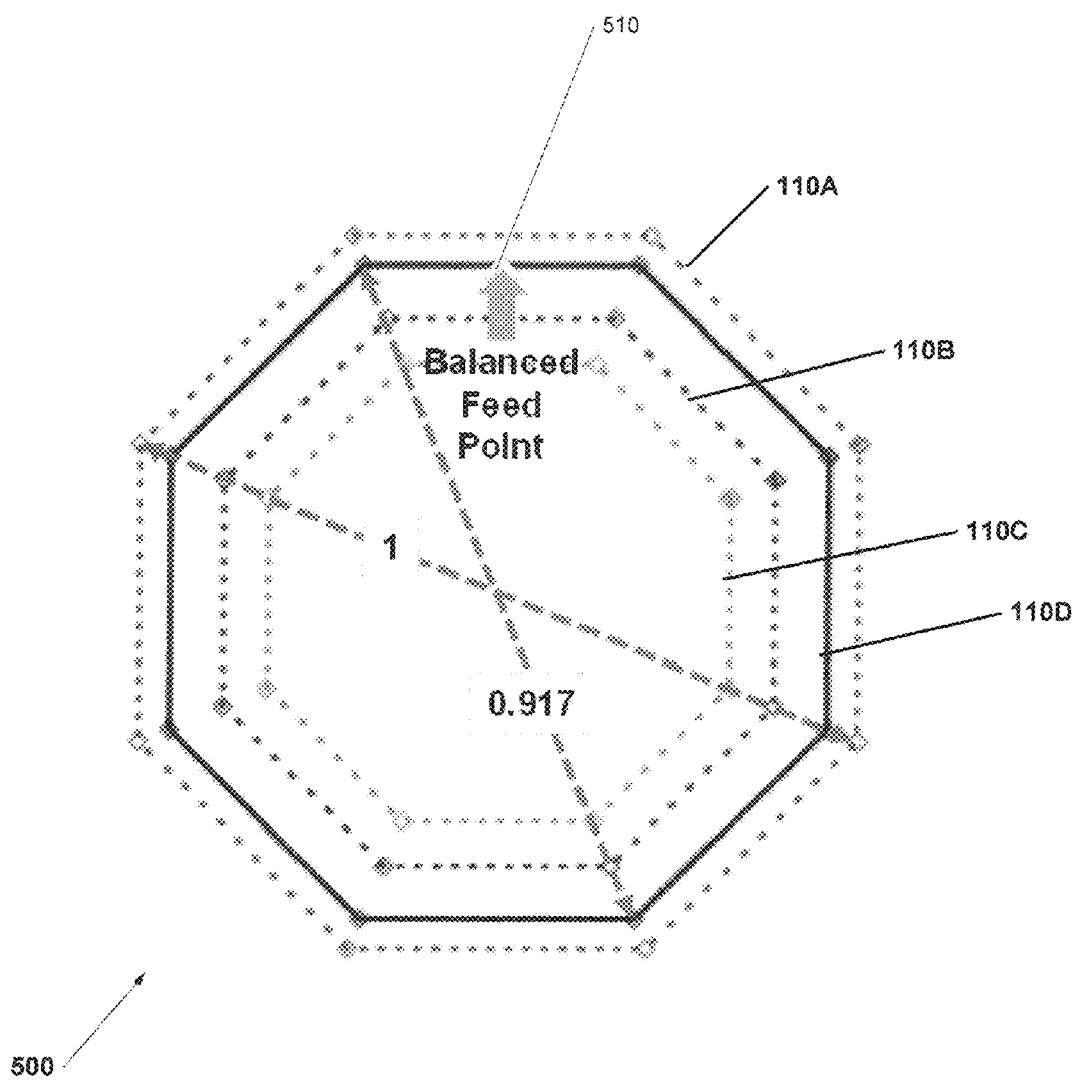
FIG. 7 illustrates an exemplary geometric relationship of a fourth loop added to the configuration of FIG. 2, in accordance with one embodiment.

Near-field sensitivity can be improved marginally through the use of more loops. That is, a probe or antenna system having one outer loop and three loops that total the area of the outer exhibits slightly better performance. This improvement occurs for a total of loops such as four, five, etc. However, in some instances, losses associated with more loops may nullify some of the improvements. In addition the volume of this improvement decreases with the increase in the number of turns. Also, for loops of any size or number, it should be noted that the use of larger conductor diameters leads to greater frequency dependency in the far-field cancellation performance. FIG. 7, discussed further herein, illustrates a configuration with four loops.

Figure 3:
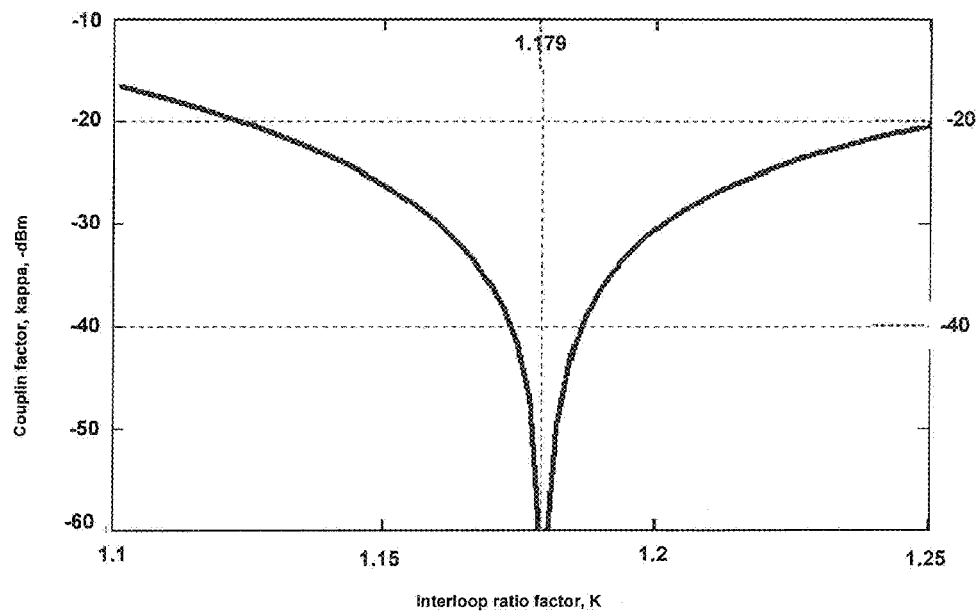
FIG. 3 is an exemplary graph showing the coupling factor (kappa) between two sets of loops as a function of an inter-loop ratio, K, in accordance with one disclosed embodiment.

The range of ratios usable to help optimize the isolation between the two sets of loops (and, thus, improve RFI suppression) can be determined, in one embodiment, analytically, using a concept of multiplexing loops within substantially the same space. In an antenna with multiple loops, it is possible to balance coupling factors between opposing parts of an antenna to decouple one part of an antenna from another part, such that the coupling from one part of one antenna loop is equal to but opposite to the coupling to another part of another loop. For example, consider an exemplary antenna having three loops, with a first loop and second and third loops that are in opposition to the first loop. This configuration can be analyzed to vary the ratios between the first loop and the second and third loops in opposition, to determine a ratio (between the first loop and second and third loops) where a null is found. FIG. 3, described further herein shows such a null (which corresponds to maximum isolation from a magnetic standpoint). After determining a ratio having maximum isolation, the ratio configuration having maximum isolation can be further refined, if needed, via mechanical or other means (e.g., turnbuckles) to compensate for any manufacturing errors or tolerances.

Note that FIG. 2 illustrates examples of specific values that optimize the isolation between the two sets of loops based on the magnetic coupling of the loops. This relationship is further illustrated in FIG. 3, which plots the coupling factor between the two sets of loops as a function of the inter-loop ratios defined by the following equation:

$$K_{outer} \equiv 1, K_{middle} \equiv \sqrt{\frac{K}{2}} \text{ and } K_{inner} \equiv \sqrt{\frac{2-K}{2}} \quad (1)$$

where K is defined to be the inter-loop ratio factor, which expresses the relationship between the relative sizes of the three loops (the sizes are relative to the size of the outermost loop (having been normalized to one (1), and all of the other sizes are relative to one).

When evaluated for the optimum value of K=1.179, shown in the plot to result in the maximum level of isolation between the sets of loops, the resultant ratios for the dimensions of the middle and inner loops are:

$$K_{middle}=0.7678 \text{ and } K_{inner}=0.6407 \quad (2)$$

It is further noted that a significant amount of tolerance is permitted in selection of the inter-loop factor, K, such that a suboptimum, but still acceptable level of isolation is achieved. For example, referring to FIGS. 2 and 3, values for K between 1.125 and about 1.25 still achieve isolation on the order of −20 dB, which is likely to allow proper operation of the electronic agility necessary to optimize the desired RFI suppression.

Additional factors to consider in designing the geometric relationship and ratios described herein include taking into account (and, advantageously, compensating for) at least some of the parasitic effects resulting from second-order capacitive coupling between the conductor loops, to help increase the isolation between the sets of loops (note that it is not always simple to determine whether a given parasitic effect arises from a primary (inductance) or secondary (capacitance) source.). Further, these parasitics can result in some frequency dependence (i.e., the optimum values and/or range for the ratios, as described herein, may vary somewhat based on the frequencies used with the antenna). However, at least some of the automated adjustment embodiments described herein offer an effective way to compensate for these often unavoidable frequency dependent effects. This is discussed more in connection with FIGS. 4 and 5 herein.

As a result of this geometric relationship (see FIGS. 2 and 3), two electrically independent ports (balanced feed ports) are available to use for the purposes of controlling the RFI response of the composite probe (antenna). Specifically, the outermost loop 110A and the innermost loop 110C are connected together in opposition to each other and driven at an appropriate point to form the first balanced feed point (port R2) 130. Additionally, the remaining middle loop 110B s also driven to provide the second, independent feed point (port R1) 120.

Figure 8:
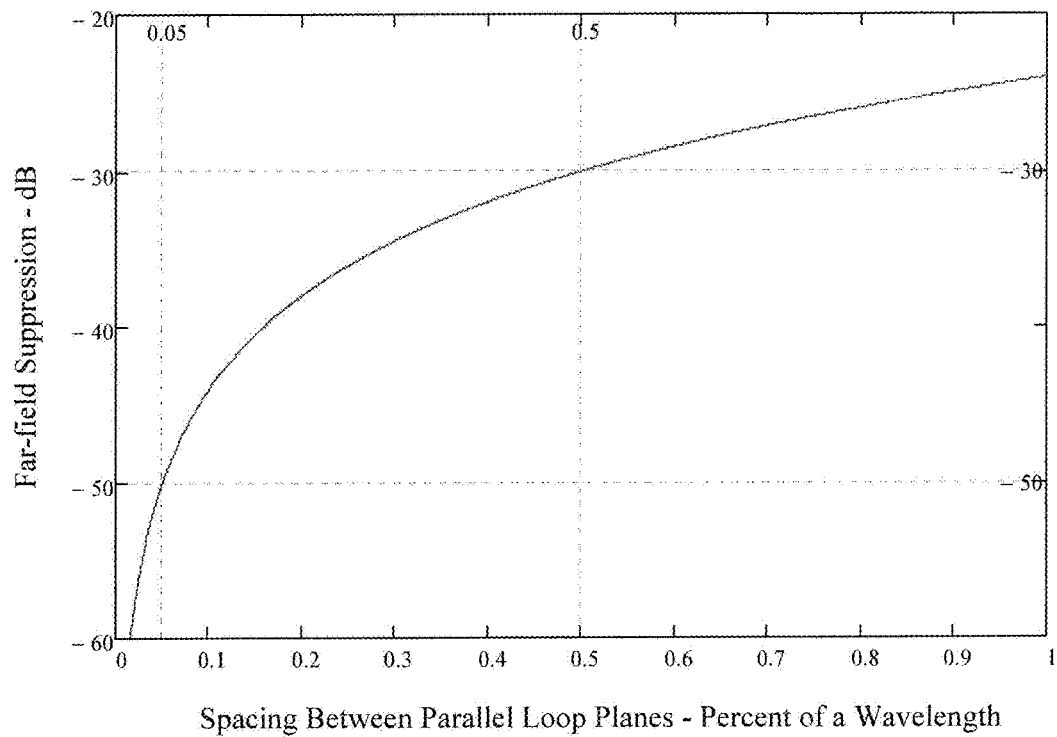
FIG. 8 is a graph showing a plot of RFI suppression as a function of spacing between loops.

As shown in FIGS. 1 and 2, in at least one advantageous embodiment, the use of substantially coplanar loops of conductors 110 is deemed optimum, but in other embodiments, configurations are provided where one or more loops are situated in a second or even a third plane, where the second or third plane is spaced apart from (but substantially parallel to) the other loop plane. However, as the spacing S between loop planes increases, the maximum achievable RFI suppression may become degraded, eventually diminishing to an unacceptable level. This effect is illustrated by equation (3) below for the situation where the plane of the largest loops is separated from that of the other two loops; while the two planes are keep parallel. In addition, FIG. 8 illustrates a plot of equation (3) for a range of spacing normalized to wavelength. This plot helps illustrate how, for a given wavelength, suppression is better the closer the loops are together and that it can degrade as spacing between loops increases.

In one embodiment, the maximum achievable RFI suppression also was found to be dependent on the relative phase difference that exists between (a) the two loops of substantially or exactly the same size, or (b) two loops having substantially or exactly equal areas (e.g., the outer loop as one set and the two inner loops as the other set). This suppression as a function of the phase difference, which is plotted in FIG. 8, is defined as follows:

$$\text{Suppression}=2\sin(\pi \text{Spacing}/\lambda) \quad (3)$$

where λ is the wavelength at the operational frequency; and where the Spacing is the spacing between either the two loops of substantially the same loop area or between a loop and the other two loops (where two of the loops, together, have the same total loop area as the other loop). In at least one embodiment, it is possible for both conditions to exist at the same time, e.g., for two loops to be substantially or exactly the same size and be spaced apart by a first spacing S1, and for the sum of the loop areas of these two loops to be the same as the total area of a third loop, which is spaced apart from the pair of loops by a second spacing S2.

For low frequencies, the spacing between planes that yields an acceptable suppression level can be reasonably large. However, at higher frequencies, a relatively small deviation from coplanar results in significantly greater degradation in the achievable RFI suppression. Note that for probes of any size, the coplanar configuration yields the maximum RFI suppression.

The illustrated geometry in the exemplary embodiment of FIG. 2 results in the difference of the area of the outermost loop 110A minus the area of the innermost loop 110C to be exactly equal to the area of the middle loop 110B (but this is not limiting; in at least one embodiment, a tolerance of about 0.1% (e.g., 60 dB of suppression), or better, is allowable). Advantageously, it is desirable in at least some embodiments to keep the tolerance as low as possible to help ensure minimum degradation of the RFI suppression, because a large deviation in tolerance limits the amount of RFI suppression.

For at least some embodiments, more mechanical variation might be tolerated based on the automated (electronic) compensation approach. For example, at least one embodiment is effective in restoring RFI suppression to near the maximum with as much as a 10% error in the mechanical system. However, it is advantageous, for some embodiments, to have a tighter tolerance on the mechanical part of the system (e.g., no more than a 1% error). Effectively, in one embodiment, an electronic cancellation feedback loop provides up to 20 dB of cancellation. Thus, the 40 dB of suppression (arising, e.g., from the geometry and arrangements described herein), in combination with the electronic cancellation feedback loop, results, in this embodiment, in a final 60 dB suppression after the application of the electronic cancellation. Further improvements or increases in mechanical suppression could result in even more final suppression, as will be appreciated. Note, however, that frequency dependent component of the errors are not as easily removed using a mechanical approach.

Thus, when the RFI responses present at the two independent ports (i.e., the balanced feed point R1 and the balanced feed point R1 of FIG. 2) are summed, with the appropriate phasing, the resulting RFI output from the summer circuit is therefore substantially minimized. Introducing an electronic means of adjusting the amplitude and phase of one of these responses, as discussed further herein, thereby yields a means of automating the control of the RFI rejection performance. Such an implementation is illustrated in the functional block diagram of FIG. 4.

Figure 4:
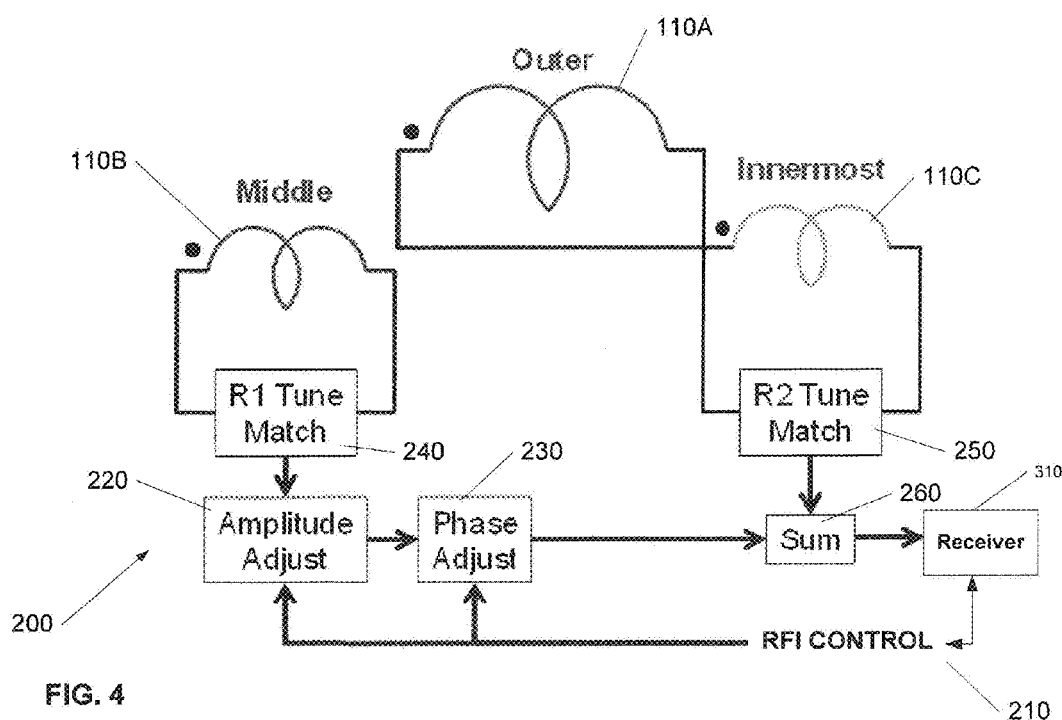
FIG. 4 illustrates an exemplary functional block diagram of an automated control system, in accordance with one embodiment.

Before discussing FIG. 4, it must be is noted that the linear geometric ratios of 1:0.7678:0.6407 (also referred to herein as inter-loop ratios) are not dependent on the actual shape of the respective loops, as long as the shapes are all substantially similar. That is, the two port independence is maintained using these ratios for round, square, rectangular or any other multi-sided polygonal shape, as long as all of the conductor loops have substantially or exactly the same shape. Even non-polygonal shapes (e.g., circles, ellipses, etc.) can be implemented while maintaining this two port independence, if these ratios are substantially maintained.

Figure 5:
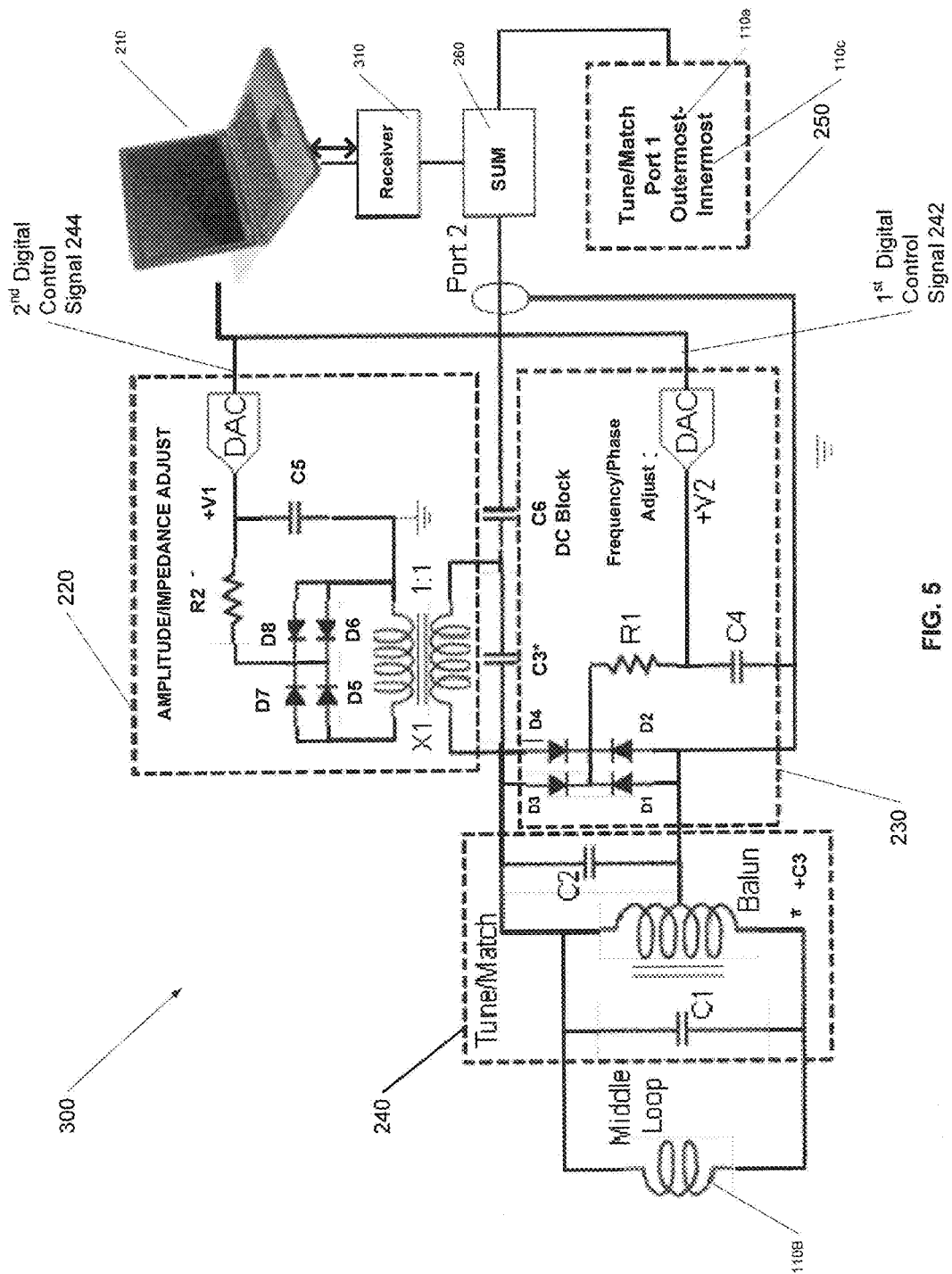
FIG. 5 illustrates an exemplary schematic of the automated control system implementation of FIG. 4, in accordance with one embodiment.

It also should be understood that the linear geometric ratios of 1:0.7678:0.6407 (as shown in FIGS. 2 and 3, e.g.) are not limiting. In at least one embodiment, these linear geometric ratios can have up to a 10% tolerance (as noted above in connection with the discussion of FIGS. 2 and 3), but the more the geometric ratio reaches the tolerance limit, the greater the likelihood that the tolerance associated with the electronic controls (described further herein in connection with FIG. 4) would be reduced. Even if isolation is smaller than 20 dB (e.g., isolation of 15 dB), the two sets of loop antennas (i.e., the middle loop 110B and the set containing the inner loop 110C and outer loop 110A) are, in one embodiment, independent enough for proper operation as independent ports that are able to be summed as shown in FIGS. 4 and 5 (described further herein). This level of isolation of 15 dB still provides two independent samples of noise, such that one can constructively interfere one sample of noise with the other sample of noise, to help to cancel out the noise.

Further, it is noted that the use of mixed shapes is possible, though the exact geometric relationship required to maintain port independence changes dependent on the relative areas and shapes being used. Therefore, it is seen that at least some of the embodiments described herein apply equally to such a set of conditions as part of its implementation in at least those embodiments. Further, extending the concept to a set of more than three loops is also possible by adjusting the appropriate ratios of one loop or set of loops in respect to a second set of loops.

FIG. 4 is an illustrative functional block diagram of an automated control system 200, in accordance with one embodiment, and FIG. 5 illustrates an exemplary schematic 300 of a circuit implementing the automated control system 200 of FIG. 4. That is, FIG. 5 provides further exemplary details as to the how the functional blocks of FIG. 4 are implemented.

Referring to FIGS. 4 and 5, a possible implementation of an automated control scheme for the three loop configuration described above is illustrated in the schematic 300 shown in FIG. 5. The functional diagram 200 of FIG. 4 and the schematic 300 of FIG. 5 both include a tune/match network 240 for port 2 (associated with middle loop 110B), a tune/match network 250 for port 1 (associated with the set containing outermost loop 110A and innermost loop 110C), an amplitude/impedance adjust block 220, a frequency/phase adjust block 230, a summer circuit 260 (also referred to herein as a sum port), a receiver 310, and a computer/controller 210. Note that, although the computer/controller 210 is shown for illustrative purposes (in FIG. 5) as a laptop computer, the embodiments disclosed herein are not limited to using laptop computers. Any type of computer, controller, or other apparatus, whether implemented in software or hardware, that is capable of generating the required inputs and responding to the outputs, as generated and/or required by other parts of the circuit of FIGS. 4 and 5, is usable as the computer/controller 210.

The exemplary automated control system 300 of FIG. 5 is associated with the exemplary geometry of FIG. 2, so there is a tuning/matching circuit for each of the sets of loops (where each subset of loops in FIG. 2 is associated with a respective port, e.g., outer loop 110A and inner loop 110C are associated with port 2 (balanced feed point R2) and middle loop 110B is associated with port 1 (balanced feed point R1). Note that, in FIG. 5, for the sake of compactness of the drawing, only the tune/match network 240 (for the middle loop 110B, associated with port 2) is shown in detail, but it will be understood that the tune/match block 250 (for port 2, associated with the set of loops that includes outermost loop 110A and innermost loop 110C), is substantially similar to the illustrated tune/match block 240, except that it does not necessarily need the electronically variable components (i.e., diodes, DACs and computer control) implemented in block 240. In at least one embodiment, however, the tune/match block 250 does include electronically variable components.

Referring to tune/match block 240, it includes a capacitor C1, a Balun, and a capacitor C2. This tune/match block 240 is actually made adjustable via the network of diodes D1 through D4, which effectively act as a parallel capacitance (as described further below). The frequency/phase adjustment in this block results from the total of the value of capacitor C2 plus the effective capacitance of the diodes (D1 through D4) as they are biased by the control voltage +V2 from the DAC in block 230, which is coupled to $1^{st}$ digital control signal 242. The impedance amplitude is controlled by the diodes D5-D8 in block 220. In addition, still referring to tune/match block 230 and amplitude/impedance adjust block 220, the notation "+C3" is there to indicate that the actual C3 capacitor (which is denoted with an asterisk in block 220) is effectively part of the function of the tune/match block 240.

Referring now to the frequency/phase adjust bock 230, it includes four diodes D1, D2, D3, D4, resistor R1, capacitor C4 (which acts to shunt the RF to ground), capacitor C6 (which acts as a DC blocking capacitor), and a Digital-to-Analog converter (DAC) (note that although the actual capacitor C6 is not within the dotted line around the frequency/phase adjust block 230, this capacitor is part of the frequency/phase adjust block; for clarity in the image, the dashed line was not drawn in a manner that would cause it to pass through the actual components being illustrated). The diodes D1, D2, D3, and D4 act as variable capacitive diodes, to provide a means of varying the resonant frequency of the L-section match of the middle loop 110B (via tune/match block 240). The DAC of frequency/phase adjust block 230 receives a first digital control signal from controller/computer 210, and converts the first digital control signal to an analog bias voltage +V2 for diodes D2 through D4. That is, in frequency/phase adjust block 230, the diodes D1-D4 are actually standing in, effectively, as voltage variable capacitors. By adjusting the reverse voltage on the diodes D1 through D4, it is possible to adjust the apparent capacitance of those devices. Thus, the effective capacitance of D1 through D4 is in parallel with capacitor C2 of tune/match block 240.

In addition to providing a fixed, coarse tune of the system of FIG. 5, the tune/match block 240 also provides a phase matching function (note that the other blocks of FIG. 5 help to provide fine tune adjustments to the system of FIG. 5). Within the 3 dB bandwidth of the middle loop 110B, when matched to the terminal impedance of receiver 350 (e.g., 50 ohms), the relative phase of the antenna's current can also be controlled by minor adjustments of the bias voltage V2 supplied to these diodes D1 through D4, without substantially affecting the impedance of the port (port 2), thereby providing a control of the response phase from port 1. By varying the bias voltage V2, and thus varying the capacitance, it is possible (e.g., via controller/computer 210) to change the resonant frequency of the middle loop 110B a small amount. Within the bandwidth of the middle loop 110B, the tune/match block 230 has a bandpass response, and within that bandpass response, adjusting the actual resonant frequency within the bandpass changes the phase of the current coming out of that middle loop 110B.

For example, adjusting the circuit's resonance such that it is one half the tuned probe's bandwidth away from the desired operating frequency causes the phase of the current to be 45 degrees out with the voltage at the feed point. This also affects the terminal impedance of the circuit, but the amount of phase control required to match the phases of the currents in the two parts of the probe is small, assuming geometric tolerances are maintained through manufacture and/or via geometric fine adjustments as previously described. Therefore, the effect on amplitude will be minor, making the two functions substantially independent. Further, second order adjustment of the opposite functions can be applied to further minimize the sum response. Thus, the phase response of the resulting current can be changed within the bandpass of the probe. In addition, within a narrow bandwidth (e.g., an exemplary antenna bandwidth of 50 kHz), the adjustments described herein have a fine enough granularity to be used to adjust phase and amplitude.

Although not illustrated in FIG. 5, the tune/match block 250 for the set of loops that includes innermost loop 110C and outermost loop 110A functions in a manner similar to that described for the tune/match network 240 for middle loop 110B. As shown in FIG. 4, it does not assume the use of electronic tuning elements, though, in at least some embodiments, such elements could be applied to it as well.

In a further embodiment, any one or more of the adjustment blocks (i.e., any or blocks 220, 230, 240, 250 in the system 300 of FIG. 5) could be implemented wholly or partially using a mechanical adjustment for a given frequency (e.g., similar to or adapted from methods and apparatuses described in the aforementioned '791 and '242 patents). There could be a mix, for example the middle loop 110B could have mechanical adjustment and the inner loop 110C and outer loop 110A could have electrical adjustment (or vice versa).

Although not shown in FIG. 5, it will be appreciated that, in some embodiments, any one or more of the elements shown therein can be replaced by adjustable or step elements, to enable tuning to a wider frequency band.

Referring again to FIGS. 4 and 5, and to the amplitude/impedance adjust block 220, in a similar manner to that described above for diodes D1 through D4, the set of diodes, D5-D8, control the terminal impedance of Port 2. A second control signal is received at the DAC of the amplitude/impedance adjust block 220, and converted to an analog bias voltage +V1, which is used to bias the diodes D5 through D8. The 1:1 transformer X1 acts as a DC block, to keep the biasing voltage (used to bias the diodes D5 through D8) from crossing the transformer and affecting the rest of the circuit, so the effect is that the effective capacitance of the diodes D5 through D8 is in parallel with C3, and thus operates to vary the effective series capacitance presented to the rest of the circuit. Varying the effective series capacitance primarily varies the impedance level presented by the amplitude/impedance adjust network 220. By varying the net series capacitance, only the impedance from 40-60 ohms is affected substantially. If needed, an optional trimmer capacitor could be added to block 220 to get the impedance to the starting value of 40 ohms.

For example, in one embodiment, the trimmer capacitor helps to bring the unadjusted terminal impedance to be close enough to the desired output impedance such that the diodes D5 in through D8 have sufficient capacitance to affect sufficient control over the output impedance. The output impedance level is commonly 50 ohms, but this is not limiting; depending on the desired design level, other impedance levels (e.g., 75 ohms or 300 ohms or even 600 ohms) are possible. For example, one way of implementing the SUM is to tune each circuit to 100 ohms and then simply connect them in parallel, yielding an output level of 50 ohms. Another alternative is to match each to 25 ohms and connect them in series to give 50 ohms.

Adjusting the impedance level to create a minor amount of impedance mismatch (via amplitude/impedance adjust 220), in effect, causes a change in the total energy delivered to the receiver 350 from Port 2, thereby providing a means of adjusting the amplitude of the response from this port. The control voltages are adjusted by the controller, controlling computer, microprocessor or microcontroller 210 in such a manner as to minimize the total energy received by the system when the sensing system's excitation signal is not being applied. This can be done at various times throughout the sensing cycle as is found necessary (including but not limited to periodically, continuously, in response to an external command or request, etc.) in any given operational scenario.

The adjustments described above for FIGS. 2-5 provide an additional degree of freedom for operation, as compared to the '242 patent, the '791 patent, and other prior art. In one embodiment, the middle loop 110B forms an entirely separate antenna, which in the NQR realm would be viewed as a probe, because it is near field and is not radiating in the antenna sense. The other two loops (outer loop 110A and inner loop 110C) are in electrical opposition to middle loop 110B, so the result is two substantially isolated ports (R1 and R2, as shown in FIGS. 4 and 5). Thus, one of the isolated ports R1, R2 could be shorted and there would be no impact on the other port. Similarly, one of the ports R1, R1, could be left open-circuited, and there would be no change in the impedance characteristics of the other port. Thus, the two ports of FIGS. 4 and 5 are substantially independent of each other (e.g., to a $3^{rd}$ or $4^{th}$ order). The effect of this, during simulation and testing, is to result in approximately 50 dB of isolation (assuming that adjustments can be made to the circuit of FIGS. 4 and 5, to compensate at least partially for parasitics, such as parasitic capacitance. If parasitic capacitance is not adjusted for, the isolation might be closer to 30 dB, which still results in middle loop antenna 110C being substantially independent from and isolated from inner antenna 110C and outer antenna 110A.

It should be noted that, in at least some embodiments, there is an assumption that, in addition to the electrical adjustments described herein, there also is some mechanical adjustment (which can, in some embodiments, be done prior to the electrical adjustment) to ensure that isolation between the sets of loops is at least at a minimum level of 15-20 dB from just the mechanical isolation alone. This initial "mechanical" level of isolation between the two ports is not controlled by that functional block diagram FIG. 4, in the disclosure. Rather, the functional block diagram of FIG. 4 is more related to automatic adjustment of the RFI response.

Figure 6A:
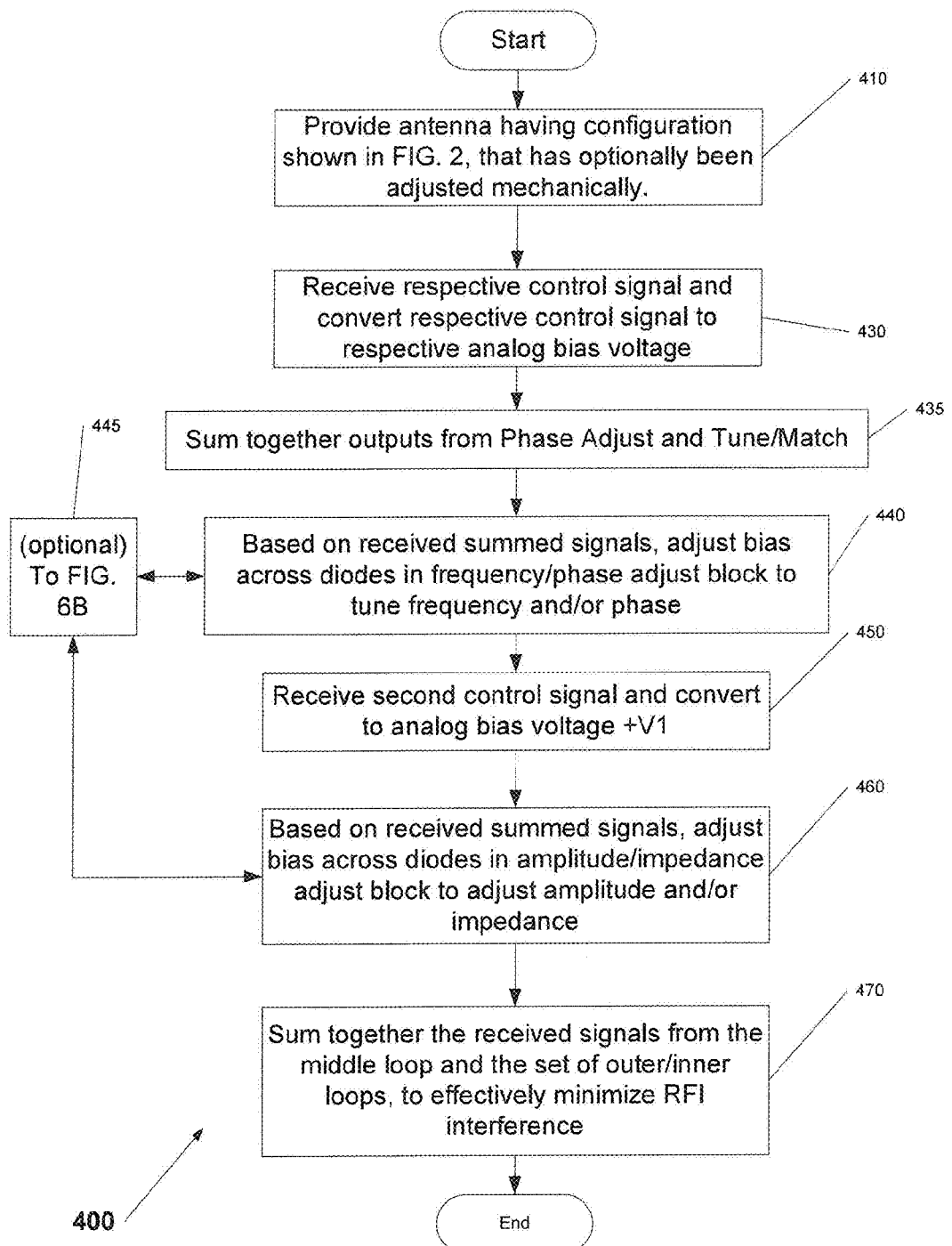
FIG. 6A is a first flowchart of a method for electronic adjustment to reduce RFI, in accordance with one embodiment.
Figure 6B:
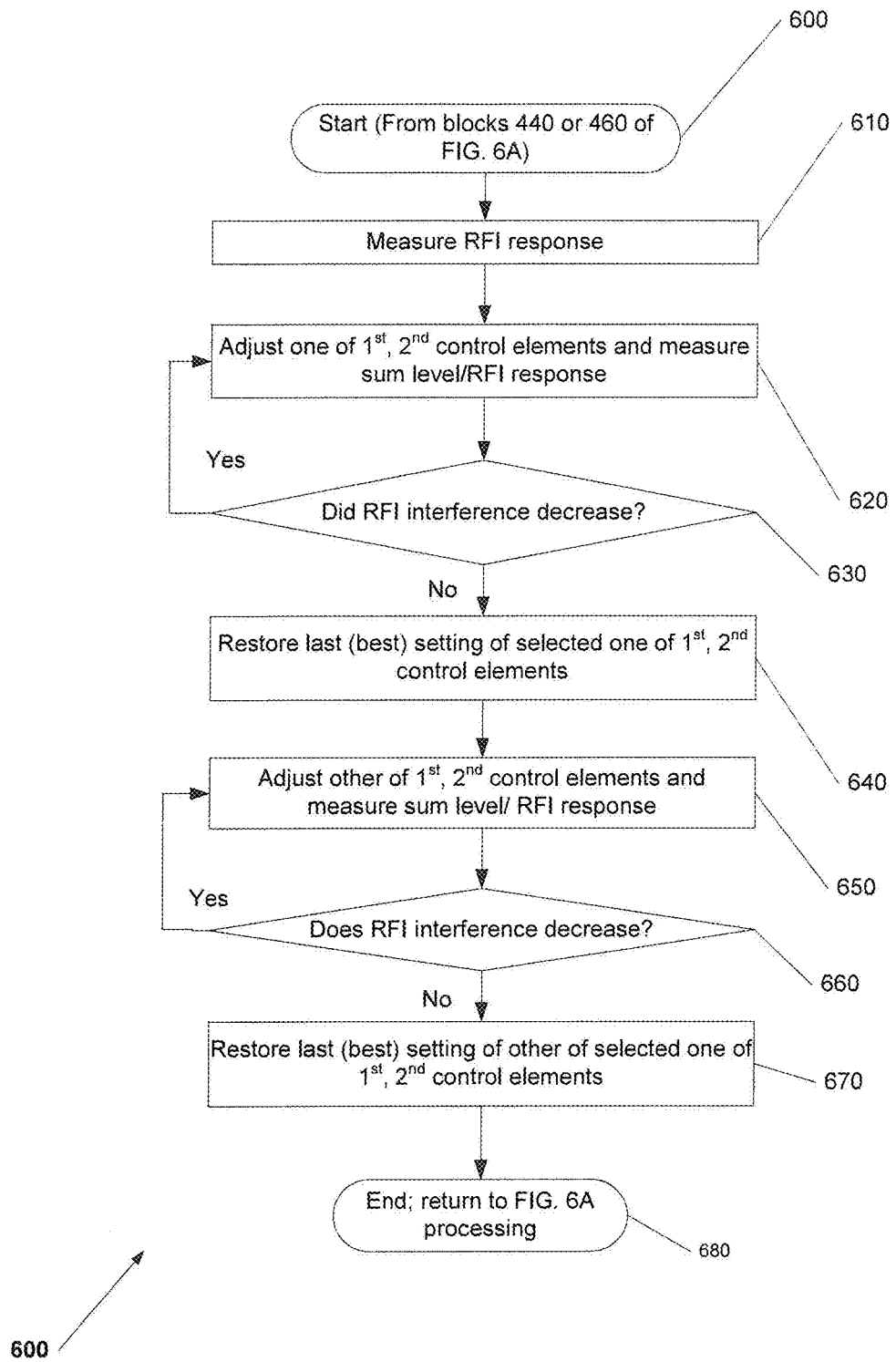
FIG. 6B is a second flowchart showing optional processing associated with one step of FIG. 6A.

FIG. 6A is a first flow chart 400 of a method of automatically controlling the antenna configuration of FIG. 2, using the circuit of FIGS. 4-5, in accordance with one embodiment, and FIG. 6B is a second flow chart 600 showing optional processing associated with one of the steps of FIG. 6A. Referring to FIG. 6A, an antenna is provided having the configuration shown in FIG. 2 (block 410). The respective received control signal, for the given antenna loop set, is received and converted to an analog bias signal (block 430). Based on the sum of the signals received at sum circuit/sum port 260, further control signals are generated to adjust the bias voltage across the diode block D1 through D4, to tune frequency and/or phase (block 440). Optionally, this tuning can include processing steps intended to minimize RFI interference (block 445 and FIG. 6B, discussed further herein).

Referring still to FIG. 6A, another control signal is received (block 450) and converted to analog bias voltage V1. This bias voltage V1 is used to adjust the bias voltage across diodes D5 through D8, in the amplitude/impedance adjust block, to adjust, respectively, amplitude and/or impedance (block 460). Optionally, this tuning can include processing steps intended to minimize RFI interference (block 445 and FIG. 6B, discussed further herein).

When all adjustments are complete, the received signals from the respective loops are, effectively, summed together (block 470), to result in substantial minimization of RFI.

FIG. 6B provides one optional process 600 to help to minimize the sum of block 470 of FIG. 6A, Referring to FIGS. 5, 6A, and 6B, the RFI response going into receiver 310 is measured (block 610). Next, a small adjustment is made to one of the control elements (e.g., one of the amplitude/impedance adjust or frequency/phase adjust blocks—order is not important), and RFI response is measured again (block 620). A check is made to determine if RFI interference decreases (block 630). If RFI interference decreases, processing returns to block 620 and repeats until RFI interference is no longer decreased by the adjustment. In at least one embodiment, a proportionality feature is used to determine the size of the next adjustment. At block 630, after adjustment, if RFI interference does not decrease, then the control element is returned to its last best setting (e.g., the setting the provided the best decrease in RFI interference) (block 640).

A small adjustment is made (block 650) to the other of the control elements (i.e., the one that was not adjusted in block 620), and the RFI response is again measured. If this second adjustment decreases the RFI interference (block 650), then adjustment continues (block 660) until no more decrease is reached (e.g., the RFI interference level stays substantially the same or gets worse). In one embodiment, a proportionality is used to determine the size of the next adjustment. As with the first control element adjustment, when RFI interference no longer decreases (block 660), the second control element is returned to its last, best setting (e.g., the setting that provided the best decrease in RFI interference (block 67). If this reduces the level it is done again, until the level rises, possibly using a proportionality to determine the size of the next adjustment. Then the last (best) setting is restored and the other parameter is varied and the sum level measured. Thus, the process of FIG. 6B effectively stops making adjustments when it can't effect an improvement beyond some predetermined threshold level. It will be appreciated, as well, that the process of FIG. 6B can be varied to balance accuracy, speed, and optimization.

Reference is now made to FIG. 7, which shows a geometric relationship 500 that includes a fourth conductor loop 110D to an arrangement similar to the arrangement of FIG. 2, in accordance with one disclosed embodiment. Note that, in this arrangement, the loop groupings differ from those shown in FIG. 2. The introduction of the fourth conductor loop 110D, which is substantially concentric and coplanar to the others, with a unique geometric relationship to the other three, provides a third electrically independent port which is used to instantiate a transmit function within a single, flat assembly, while the first, second, and third loops provide a receive function. In the example embodiment of FIG. 7, the fourth loop is being added to the total (composite) of the three loops previously described.

The geometric ratio of 1:0.917 results in the fourth loop 110D having a feed point 510 that is electrically independent of the sum port 260 (FIG. 5) of the three receive loops 110A, 110B, and 110C. This helps, in one embodiment, to provide a single, substantially flat antenna structure capable of working as part of a "multi-layered" approach to permit providing transmit and receive functions at substantially the same time. In such a multi-layered approach, in one embodiment, other "layers" can include frequency separation and filtering and feedback cancellation (a sample of the transmit energy is adjusted in phase and amplitude to counter the residual energy in the receive chain). In at least one embodiment, the isolation provided using at least some of the disclosure described herein is a necessary component of enabling such a substantially simultaneous receive and transmit capability.

In at least one embodiment, a means of providing mechanical adjustment of the exact area of this loop is usable, such as described in the aforementioned '242 and '791 patents, to assure the proper geometric relationship to the aggregate of the other loops 110A through 110C, such that maximum isolation between this loop and the second set of loops is achieved. As with the isolation describe above for the two parts of the far-field suppression configuration of loops, a tolerance in this ratio is permissible such that a less than optimum level of isolation is achieved that remains acceptable for the independent use of this third port. However, it is noted that reducing the isolation level results in far-field energy being coupled from this fourth loop into the composite of the other three loops, thereby degrading its far-field rejection.

In a further embodiment, if some other geometry ratios are used, for example if the two inner loops are very nearly the same size, the composite of the three loops still geometrically suppresses RFI (as long as the sum of the areas of the two smaller loops very nearly equals that of the larger). This configuration precludes using any one of them as an isolated port, but would not preclude the suppression effect. In yet another embodiment, a fourth loop can be added and sized so that it is electrically isolated from the sum of the other three loops.

It should be noted that because of the reciprocity law of passive circuits, the transmit and receive functions of the described sensor probe are interchangeable on this structure. That is, everywhere in this description and in the figures referenced herein, the word receive is used it can be replaced with transmit and likewise transmit can be replaced by receive, should the application be better served by such an arrangement. As will be appreciated, however, if transmit and receive are reversed, the suppression of RFI becomes the suppression of radiated power. Independent of the order of transmit versus receive, the described circuits are usable for suppression of far field energy, either on reception (RFI) or transmission (radiation). Thus, it should be understood that, throughout this disclosure, the figures and all description are applicable to all types of far field energy.

For example, this is true for the use of this approach in implementing a vicinity RFID interrogation system, such as those operated at 13.56 MHz in the US and many European nations. In such an application, the far-field radiation would be dramatically reduced in the excitation field using the three loop differential part of the sensor to transmit the interrogation signal and the receive sensitivity of the system would be maintained using the conventional single (fourth) loop for the receive function. Such an approach has the advantage of being able to interrogate the RFID tags at greater ranges while maintaining governmentally imposed limitations on the radiated energy that is permitted.

All of the embodiments of the antenna geometries described herein are compatible with known techniques of resonating, tuning, and/or matching of loop antennas for the purpose of coupling to transmitters and/or receivers to achieve efficient operation. For example, passive, lumped elements; such as capacitors, inductors, or transformers; could be added in series and/or parallel combinations at the feed point of any of the embodiments of the antenna to achieve a suitable drive point impedance match with conventional art amplifiers. That is, no special provisions are required to apply embodiments of the antenna to existing or future systems.

In describing and illustrating the embodiments herein, in the text and in the figures, specific terminology (e.g., language, phrases, product brands names, etc.) is used for the sake of clarity. These names are provided by way of example only and are not limiting. The embodiments described herein are not limited to the specific terminology so selected, and each specific term at least includes all grammatical, literal, scientific, technical, and functional equivalents, as well as anything else that operates in a similar manner to accomplish a similar purpose. Furthermore, in the illustrations, Figures, and text, specific names may be given to specific features, elements, circuits, modules, tables, software modules, systems, etc. Such terminology used herein, however, is for the purpose of description and not limitation.

Although the embodiments included herein have been described and pictured in an advantageous form with a certain degree of particularity, it is understood that the present disclosure has been made only by way of example, and that numerous changes in the details of construction and combination and arrangement of parts may be made without departing from the spirit and scope of the described embodiments.

Having described and illustrated at least some the principles of the technology with reference to specific implementations, it will be recognized that the technology and embodiments described herein can be implemented in many other, different, forms, and in many different environments. The technology and embodiments disclosed herein can be used in combination with other technologies. In addition, all publications and references cited herein are expressly incorporated herein by reference in their entirety.

What is claimed is:

1. An antenna system, comprising:
    a first loop antenna comprising a first conductor forming a first loop, the first loop having a first respective loop area;
    a second loop antenna spaced apart from the first loop antenna, the second loop antenna comprising a second conductor forming a second loop, the second loop antenna having a second respective loop area;
    a third loop antenna spaced apart from both the first and second loop antennas, the third loop antenna comprising a third conductor forming a third loop having a third respective loop area, wherein:
        the first and third loop antennas are operably coupled together in electrical opposition to each other, configured to be driven to form a first independent balanced feed point, and configured to be substantially electrically and magnetically isolated from the second loop antenna;
        the second loop antenna is configured to be driven from a second balanced feed point;
        the first, second and third loops are configured such that a sum of the first and second respective loop areas, at a sum port in operable communication with the first and second balanced feed points, is substantially equivalent, within a predetermined tolerance, to the third respective loop area; and
        the first and second balanced feed points are in operable communication with an automatic control system configured to automatically and independently adjust at least one of amplitude and phase for at least one of the first, second, and third loops in operable communication with at least one of the first and second balanced feed points, where each respective automatic and independent adjustment is configured to help to substantially maximize suppression of radio frequency interference (RFI) for a sum of signals from the first and second balanced feed points.

2. The antenna system of claim 1, wherein the automatic control system comprises:
   a first amplitude adjustment circuit under automatic control and in operable communication with a respective one of the first and second loops; and
   a first phase adjustment circuit under automatic control and in operable communication with a respective one of the first and second loops;
   wherein the first amplitude adjustment circuit is configured to operate independently of the first phase adjustment circuit.

3. The antenna system of claim 1, wherein the automatic control system further comprises a first tune/match adjustment circuit in operable communication with an automatic control and a respective one of the first and second loops, the tune/match adjustment circuit responsive to a first control signal configured to provide tuning of the respective one of the first and second loops, the tuning configured to adjust a resonant frequency of the respective one of the first and second loops.

4. The antenna system of claim 1, wherein the automatic control system further comprises a first tune/match adjustment circuit in operable communication with an automatic control and a respective one of the first and second loops, the first tune/match adjustment circuit configured to provide phase matching for the respective one of the first and second loops.

5. The antenna system of claim 1, wherein the antenna system is in operable communication with a mechanical control configured to adjust a size of one of the first, second, and third loops,
   wherein the adjustment provided by the mechanical control cooperates with one or more of the adjustments performed by the automatic control system, to help to substantially maximize suppression of RFI.

6. The antenna system of claim 1, wherein the first loop comprises an inner loop, the second loop comprises a middle loop, and the third loop comprises an outer loop.

7. The antenna system of claim 6, wherein, for a given inter-loop ratio factor K, the inter-loop ratios are defined as follows:

$$K_{(outer\ loop)} = 1$$

$$K_{(middle\ loop)} = \sqrt{\frac{K}{2}}$$

$$K_{(inner\ loop)} = \sqrt{\left[\frac{2-K}{2}\right]}$$

8. The antenna system of claim 7, wherein K is between about 1.125 to about 1.25.

9. The antenna system of claim 1, wherein at least two of the first, second, and third loops have substantially similar shapes.

10. The antenna system of claim 1, wherein at least two of the first, second, and third loops are substantially concentric.

11. The antenna system of claim 1, wherein at least one of the first, second, and third loops comprises a respective set of two or more sub-loops, each sub-loop having a respective sub-loop area, wherein the sum of all the respective sub loop areas in the respective set is substantially equivalent to the respective loop area of the at least one of the first, second and third loops.

12. The antenna system of claim 1, wherein the first, second and third loops are substantially coplanar.

13. The antenna system of claim 1, wherein the first and third loops are substantially coplanar and lie within a first plane, and the second loop lies within a second plane that is spaced apart from but parallel to the first plane.

14. The antenna system of claim 1, wherein:
   (a) if any two of the first, second, and third loops have substantially the same respective loop area as each other, then a first spacing S1 is defined as being between the two loops having substantially the same respective loop area; and
   (b) if the respective loop areas of any two of the first, second and third loops, when added together, form a pair of loops that together have substantially the same loop area as the remaining one of the first, second and third loops, then a second spacing S2 is defined as being between either one of the pair of loops and the remaining one of the first, second, and third loops;
   wherein at least one of S1 and S2 is selected to help to maximize RFI suppression at a given operational frequency λ, where:

$$RFI\ Suppression = 2\sin\left(\frac{\pi S}{\lambda}\right)$$

15. The antenna system of claim 1, further comprising:
   a fourth loop antenna spaced apart from the first, second, and third loop antennas, wherein the first, second, third and fourth the fourth loop antennas are substantially concentric and coplanar, wherein the fourth antenna comprises a fourth conductor forming a fourth loop that is configured to be substantially electrically and magnetically isolated from the first, second, and third loop antennas, wherein the fourth loop is configured to include a third balanced feed point that is electrically independent of the sum port of the first, second, and third loops;
   wherein the first, second, and third loop antennas are configured to instantiate a selected one of a transmit and a receive function; and
   wherein the fourth loop antennas is configured to instantiate the other of the transmit and receive functions, such that the fourth loop antenna performs a different function than the first, second, and third loop antennas.

16. A method of increasing suppression of radio frequency interference (RFI) in an antenna system comprising first, second, and third loops, the method comprising:
   sizing the first, second, and third loops such that a sum of an area defined by the inner loop and an area defined by the second loop is substantially equivalent, within a predetermined tolerance, to an area defined by the third loop;
   operably coupling the first and third loops together in electrical opposition to each other;

configuring the first and third loops to be driven from a first independent balanced feed point and to be substantially electrically and magnetically isolated from the middle loop;

configuring the second loop to be driven from a second balanced feed point; and automatically and independently adjusting at least one of amplitude and phase for at least one of the first, second, and third loops in operable communication with at least one of the first and second balanced feed points, where each respective automatic and independent adjustment is configured to help to maximize suppression of RFI for a sum of signals from the first and second balanced feed points.

17. The method of claim 16, wherein, for a given inter-loop ratio factor K, the inter-loop ratios are defined as follows:

$$K_{(third\ loop)} = 1$$

$$K_{(second\ loop)} = \sqrt{\frac{K}{2}}$$

$$K_{(first\ loop)} = \sqrt{\left[\frac{2-K}{2}\right]}$$

18. The method of claim 17, wherein K is between about 1.125 to about 1.25.

19. The method of claim 16, further comprising:

providing a fourth loop antenna spaced apart from the first, second, and third loop antennas, wherein the first, second, third and fourth the fourth loop antennas are substantially concentric and coplanar, wherein the fourth antenna comprises a fourth conductor forming a fourth loop that is configured to be substantially electrically and magnetically isolated from the first, second, and third loop antennas, wherein the fourth loop is configured to include a third balanced feed point that is electrically independent of the sum port of the first, second, and third loops;

configuring the first, second, and third loop antennas to instantiate a selected one of a transmit and a receive function; and configuring the fourth, loop antenna to instantiate the other of the transmit and receive functions, such that the fourth loop antenna performs a different function than the first, second, and third loop antennas.

20. The method of claim 17, further comprising operably coupling the antenna system to a controller, the controller comprising at least one of an automatic electronic control and a mechanical control, wherein the controller is configured to cooperate with the automatic control system to adjust at least one of the following to help maximize suppression of RFI:

(a) a size of one of the first, second and third loops;
(b) a phase of one or both of the first and second loops;
(c) an amplitude of one or both of the first and second loops;
(d) a resonant frequency of one of the first and second loops;
(e) a phase match for one of the first and second loops; and
(g) a spacing between any two of the first, second, and third loops.

* * * * *